(12) United States Patent
Demas et al.

(10) Patent No.: US 9,999,380 B1
(45) Date of Patent: Jun. 19, 2018

(54) SEGMENTED MAGNETS

(71) Applicant: Verily Life Sciences LLC, Mountain View, CA (US)

(72) Inventors: Vasiliki Demas, San Jose, CA (US); Vikram Singh Bajaj, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 525 days.

(21) Appl. No.: 14/861,901

(22) Filed: Sep. 22, 2015

Related U.S. Application Data

(60) Provisional application No. 62/053,347, filed on Sep. 22, 2014.

(51) Int. Cl.
 *A61B 5/145* (2006.01)
 *A61N 2/00* (2006.01)
 (Continued)

(52) U.S. Cl.
 CPC .......... *A61B 5/14503* (2013.01); *A61B 5/681* (2013.01); *A61N 2/06* (2013.01); *H01F 7/0231* (2013.01)

(58) Field of Classification Search
 CPC ............ A61B 5/14532; A61B 5/14546; A61B 5/1486; A61B 5/14539; A61B 5/0031
 See application file for complete search history.

(56) References Cited

U.S. PATENT DOCUMENTS 5,305,751 A * 4/1994 Chopp ................. A61B 5/0265
600/409

5,348,050 A * 9/1994 Ashton .................. B01J 19/087
210/222

(Continued)

FOREIGN PATENT DOCUMENTS

| WO | 2013030601 | 3/2013 |
|----|------------|--------|
| WO | 2013173235 | 11/2013 |
| WO | 2014079505 | 5/2014 |

OTHER PUBLICATIONS

International Searching Authority, International Search Report and Written Opinion for International Application No. PCT/US2014/054321 dated Dec. 17, 2014, 14 pages.

*Primary Examiner* — Eric Winakur
(74) *Attorney, Agent, or Firm* — McDonnell Boehnen Hulbert & Berghoff LLP

(57) ABSTRACT

A variety of wearable magnetic assemblies are provided that are configured to produce magnetic fields having high field magnitudes and/or high field gradients. Such magnetic assemblies include a plurality of magnetic segments arranged in a linear array. Individual magnetic segments of the magnetic array can each include multiple magnetic elements. An individual magnetic segment can include elements that have similar shape, size, composition, and relative location to elements of neighboring magnetic segments while having magnetic moments that are antiparallel to the magnetic moments of corresponding elements of the neighboring magnetic segments. These wearable magnetic assemblies are configured to exert forces on magnetic particles disposed in a portion of subsurface vasculature to attract, slow, speed, separate, or otherwise influence the magnetic particles in various applications. The magnetic particles can be configured to bind to an analyte of interest.

18 Claims, 12 Drawing Sheets

(51) Int. Cl.
  *A61N 2/06* (2006.01)
  *A61N 2/02* (2006.01)
  *A61B 5/00* (2006.01)
  *H01F 7/02* (2006.01)

(56) References Cited

U.S. PATENT DOCUMENTS

| | | | |
|---|---|---|---|
| 5,978,694 A * | 11/1999 | Rapoport | G01R 33/16 600/309 |
| 6,292,680 B1 | 9/2001 | Somogyi et al. | |
| 7,357,862 B2 * | 4/2008 | White | C02F 1/481 210/222 |
| 7,951,061 B2 | 5/2011 | Foreman et al. | |
| 8,368,396 B2 | 2/2013 | Ueda | |
| 8,409,415 B2 | 4/2013 | Liu | |
| 8,529,428 B2 | 9/2013 | Creighton | |
| 8,569,044 B2 | 10/2013 | Hoon | |
| 8,624,592 B2 | 1/2014 | Lee | |
| 2006/0238194 A1 | 10/2006 | Gleich | |
| 2008/0277352 A1 * | 11/2008 | White | C02F 1/481 210/222 |
| 2009/0299127 A1 | 12/2009 | Rudolph et al. | |
| 2010/0204674 A1 | 8/2010 | Forbes et al. | |
| 2010/0264090 A1 | 10/2010 | Ellis et al. | |
| 2011/0301633 A1 | 12/2011 | Muck et al. | |
| 2012/0078068 A1 | 3/2012 | Ulmer | |
| 2012/0289764 A1 | 11/2012 | Murakami | |
| 2013/0144134 A1 | 6/2013 | Lee et al. | |
| 2013/0253550 A1 | 9/2013 | Beisel et al. | |
| 2013/0316355 A1 | 11/2013 | Dryga et al. | |
| 2013/0342205 A1 | 12/2013 | Prado et al. | |
| 2013/0344507 A1 | 12/2013 | Stilwell et al. | |
| 2014/0005522 A1 | 1/2014 | Zurovcik | |
| 2014/0021105 A1 | 1/2014 | Lee | |
| 2014/0170201 A1 | 6/2014 | Levy et al. | |

* cited by examiner

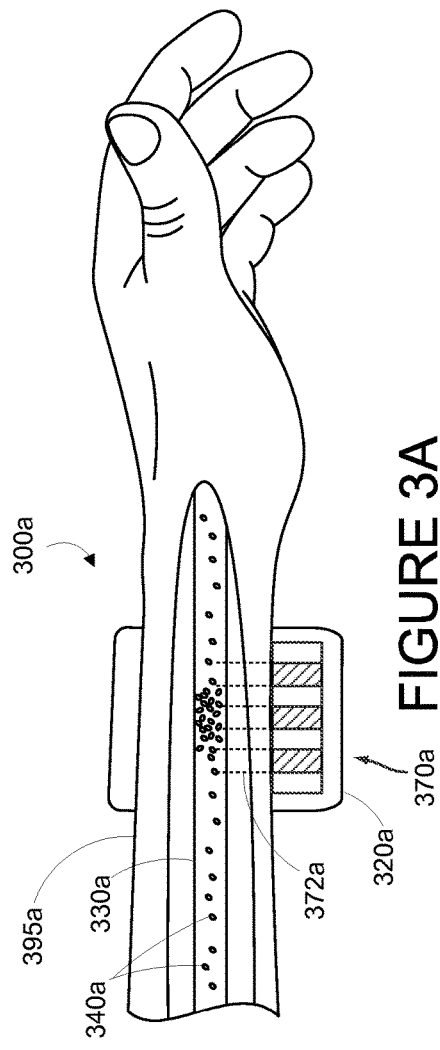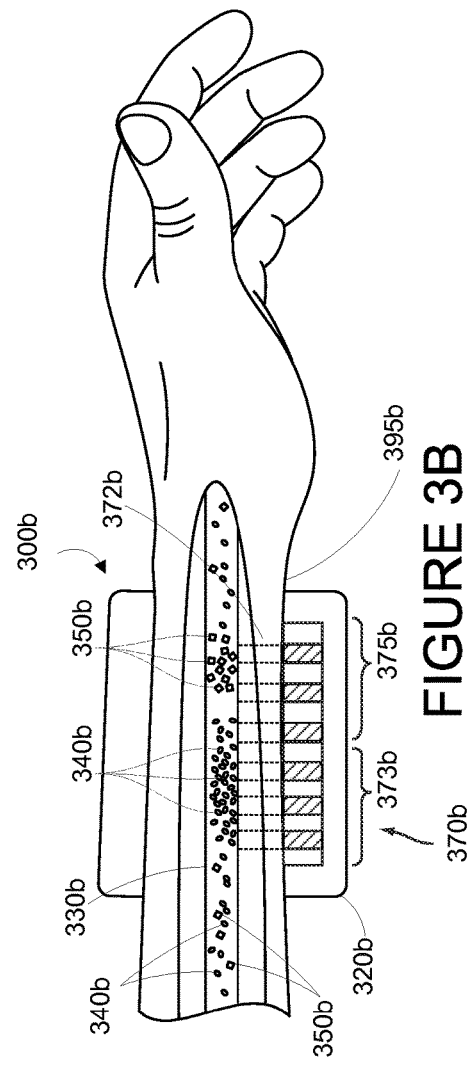

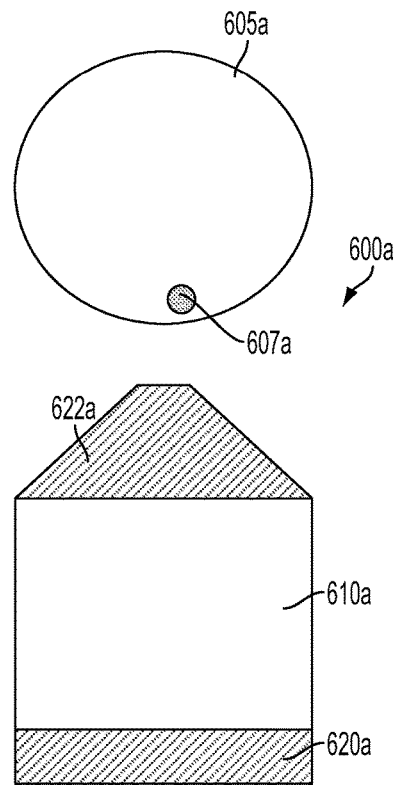 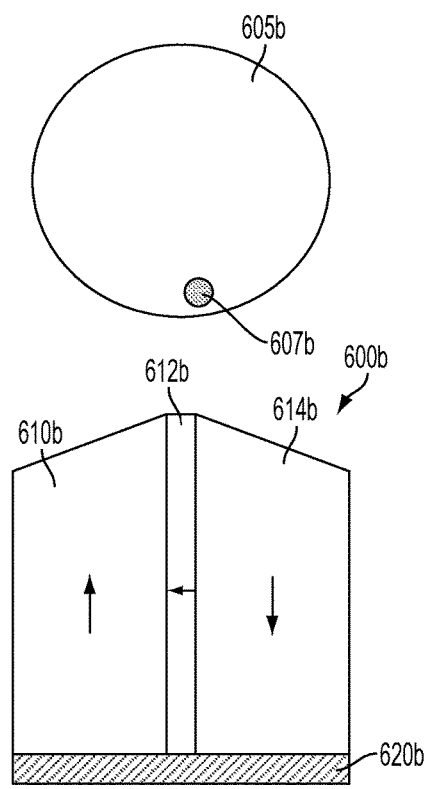
FIG. 6A    FIG. 6B
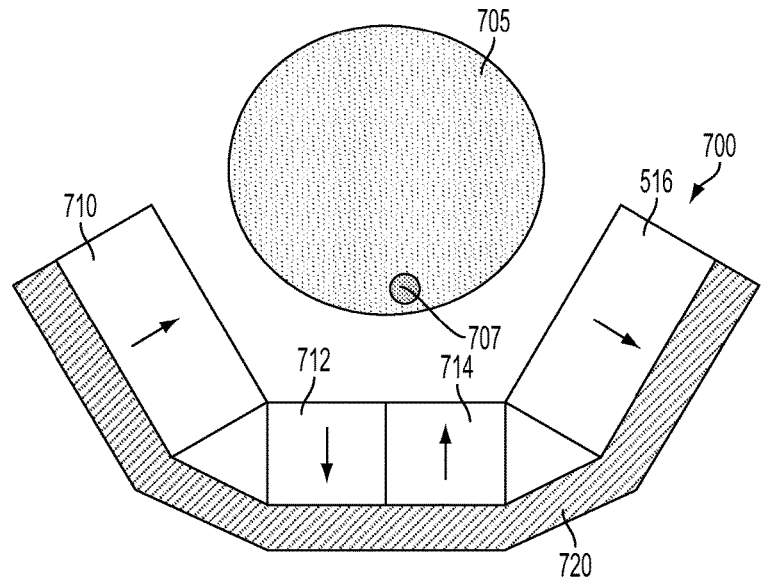
FIG. 7

SEGMENTED MAGNETS

CROSS-REFERENCE TO RELATED APPLICATION

This application claims priority to U.S. Provisional Patent Application No. 62/053,347, filed Sep. 22, 2014, which is incorporated herein by reference.

BACKGROUND

Unless otherwise indicated herein, the materials described in this section are not prior art to the claims in this application and are not admitted to be prior art by inclusion in this section A number of scientific methods have been developed to detect, measure, collect, modify, and/or affect one or more analytes in a biological or other environment. The one or more analytes could be any analytes that, when present in or absent from a person's body, or present at a particular concentration or range of concentrations, may be indicative of a medical condition or health state of the person. The one or more analytes could be substances whose distribution, action, or other properties, interactions, or activities throughout an animal's body is of scientific or medical interest. The one or more analytes could include pharmaceuticals or other substances introduced into the biological or other environment to effect some chemical or biological process. The one or more analytes could be present in living or nonliving human or animal tissue, and could be detected, measured, of affected in an in vivo, ex vivo, in vitro, or some other type of sample. The one or more analytes could include enzymes, reagents, hormones, proteins, drugs, nanoparticles, pharmaceuticals, cells or other molecules.

SUMMARY

Some embodiments of the present disclosure provide a device including a magnetic assembly comprising a plurality of magnetic segments, wherein the plurality of magnetic segments are arranged in a linear array, wherein the magnetic segments are separated from each other by respective specified distances, wherein each magnetic segment comprises two or more magnetic elements each having a respective magnetic moment, wherein the magnetic assembly is configured to be positioned proximate to an external body surface such that the magnetic assembly exerts a magnetic force on magnetic particles in a portion of subsurface vasculature proximate to the external body surface, wherein a first magnetic segment of the plurality of magnetic segments is next to a second magnetic segment of the plurality of magnetic segments, and wherein the magnetic moments of respective first and second magnetic elements of the first magnetic segment are each oriented antiparallel to the magnetic moments of respective corresponding first and second magnetic elements of the second magnetic segment.

Some embodiments of the present disclosure a method, including: (i) positioning a device comprising a magnetic assembly proximate to an external body surface that is proximate to a portion of subsurface vasculature, wherein the magnetic assembly comprises a plurality of magnetic segments, wherein the plurality of magnetic segments are arranged in a linear array, wherein the magnetic segments are separated from each other by respective specified distances, wherein each magnetic segment comprises one or more magnetic elements each having a respective magnetic moment, wherein a first magnetic segment of the plurality of magnetic segments is next to a second magnetic segment of the plurality of magnetic segments, and wherein the magnetic moments of respective first and second magnetic elements of the first magnetic segment are each oriented antiparallel to the magnetic moments of respective corresponding first and second magnetic elements of the second magnetic segment; and (ii) exerting, by the magnetic assembly in the positioned device, a magnetic force on magnetic particles disposed in the portion of subsurface vasculature.

Some embodiments of the present disclosure a system, including: (i) means for positioning a device comprising a magnetic assembly proximate to an external body surface that is proximate to a portion of subsurface vasculature, wherein the magnetic assembly comprises a plurality of magnetic segments, wherein the plurality of magnetic segments are arranged in a linear array, wherein the magnetic segments are separated from each other by respective specified distances, wherein each magnetic segment comprises one or more magnetic elements each having a respective magnetic moment, wherein a first magnetic segment of the plurality of magnetic segments is next to a second magnetic segment of the plurality of magnetic segments, and wherein the magnetic moments of respective first and second magnetic elements of the first magnetic segment are each oriented antiparallel to the magnetic moments of respective corresponding first and second magnetic elements of the second magnetic segment; and (ii) means for exerting, by the magnetic assembly in the positioned device, a magnetic force on magnetic particles disposed in the portion of subsurface vasculature.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 3A is side partial cross-sectional view of an example wrist-mounted device, while on a human wrist.

FIG. 3B is side partial cross-sectional view of an example wrist-mounted device, while on a human wrist.

FIG. 6A is cross-sectional view of an example magnetic segment, while positioned near a lumen of subsurface vasculature.

FIG. 6B is cross-sectional view of an example magnetic segment, while positioned near a lumen of subsurface vasculature.

FIG. 7 is cross-sectional view of an example magnetic segment, while positioned near a lumen of subsurface vasculature.

DETAILED DESCRIPTION

Figure 1A:
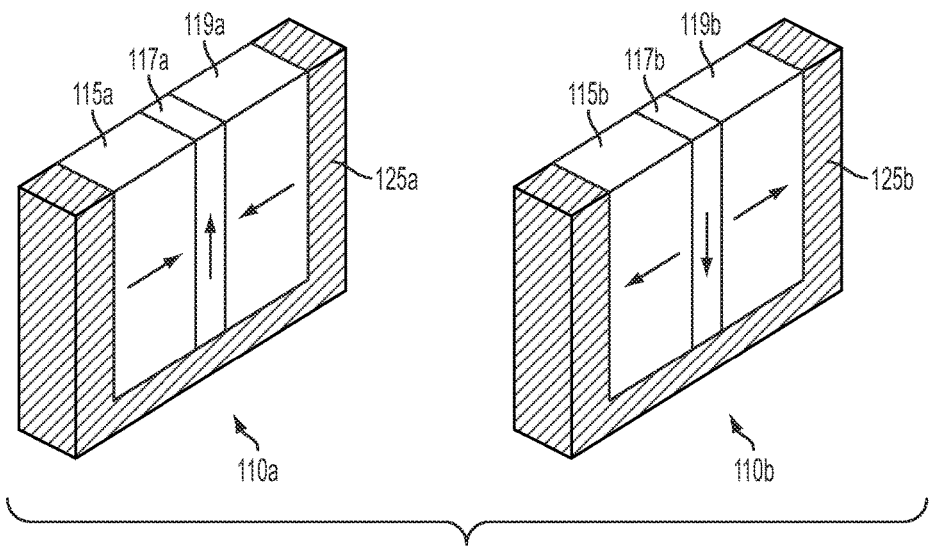
FIG. 1A is a perspective view of two example magnetic segments.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

Magnetic particles can be configured to selectively bind with an analyte of interest. Magnetic particles configured in this way can enable manipulation of, detection of, or other interactions with the analytes by applying magnetic forces to the magnetic particles. Additionally or alternatively, an analyte of interest could be intrinsically magnetic, or could be an engineered analyte (e.g., a pharmaceutical) that has a magnetic property and/or that is bound to a magnetic particle and that can be introduced into an environment according to an application.

Manipulation of, detection of, or other interactions with magnetic particles as described herein can involve magnetic fields having specified properties. In some examples, it can be desirable to direct a magnetic field of a specified large magnitude into a biological environment (e.g., within vasculature of a person's wrist). Additionally or alternatively, it can be desirable to provide a magnetic field having a specified large magnitude of magnetic field gradient. For example, a magnetic field gradient could be used for collection of, partitioning of, or application of force to magnetic particles in a viscous and/or flowing fluid (e.g., blood in a portion of subsurface vasculature of a person). Further, in some applications it can be desirable to generate these magnetic fields using relatively small, low-power devices.

Embodiments herein relate to magnetic assemblies composed of arrays of magnetic segments. A set of magnetic segments could be assembled (e.g., stacked neighboring each other and separated by respective distances, separated by one or more spacers disposed between respective neighboring segments, disposed in a housing) into a curved or straight linear array (i.e., the individual magnetic segments could be disposed substantially along a long axis of the linear array) or arranged into a branching, two-dimensional, three-dimensional, or otherwise configured array of magnetic segments. Individual magnetic segments of a magnetic assembly could individually include one or more magnetic elements (i.e., permanent magnets, electromagnets, and other components that have and/or can be operated to have a magnetic dipole moment) and that are configured to generate high-strength magnetic fields (i.e., magnetic fields having a high field magnitude and/or field gradient magnitude). The magnetic segments of a magnetic assembly could be repeated (i.e., could be identically configured), could be configured to have magnetic elements of alternating magnetic moment orientation (i.e., neighboring magnetic segments could include similarly sized and shaped magnetic elements disposed similarly within the magnetic segments and having respective magnetic moments that are substantially antiparallel), or could be configured according to some other application. Segmentation of magnetic elements in such a magnetic assembly could allow for the production of a greater magnetic field magnitude and/or greater magnetic field gradient magnitude in a target environment than could be produced by an alternative magnetic assembly having a similar size, area, mass, or other property.

These embodiments could be applied to manipulate magnetic particles in living (e.g., blood of a living human or animal) or nonliving (e.g., a sample in a container configured to enable imaging or measurement of the sample) biological environments or non-biological environments (e.g., a fluid that is part of a chemical synthesis process). In some embodiments, the magnetic assemblies could be part of a wearable device (e.g., a device configured to be worn around the wrist or other body portion). Additionally or alternatively, elements of these magnetic assemblies could be implanted or otherwise emplaced within a human or animal body (e.g., to wholly or partially encircle a portion of subsurface vasculature or other portion of anatomy of interest).

A magnetic segment of a magnetic assembly could include one or more magnetic elements. The one or more magnetic elements could be configured to produce high-strength magnetic fields. The one or more magnetic elements could be permanent magnets. Example permanent magnets include, without limitation, samarium-cobalt magnets, neodymium magnets, rare earth magnets, alnico magnets, ferrites, or other ferromagnetic or otherwise permanently magnetic materials. The one or more magnetic elements could have a variety of orientations (e.g., directions of the magnetic moment of the one or more magnetic elements) relative to a target environment and relative to each other. In some examples, the one or more magnetic elements are oriented toward the target environment. In some examples, the one or more magnetic elements include two magnetic elements having opposite magnetic orientations. In some examples, the one or more magnetic elements include three or more magnetic elements arranged as a Halbach array (i.e., a substantially locally linear or planar array wherein adjacent magnetic elements have magnetic orientations rotated by 90 degrees relative to each other, and wherein at least one of the magnetic elements of the array has a magnetic orientation perpendicular to the plane or line of the planar or linear array, respectively) in order to increase the magnitude of the magnetic field and/or magnetic field gradient on one side of the three or more magnetic elements and reduce the magnitude of the magnetic field and/or magnetic field gradient on the opposite side of the three or more magnetic elements. In some examples, a magnetic segment could have a cylindrical configuration, including an axial magnetic element having a magnetic moment oriented toward a target environment and substantially parallel to a central axis of the axial magnetic element. Such a magnetic segment could additionally include a plurality of radial magnetic elements having respective magnetic moments oriented toward the central axis and disposed surrounding the axial magnetic element.

In some embodiments, a magnetic assembly and/or magnetic segments thereof could include one or more magnetic shims or poles, i.e., elements configured to provide a high-permeability region to modify the direction, strength, or other properties of the magnetic field generated by the magnetic assembly and/or magnetic segments thereof. The magnetic shims or poles could have a variety of geometries according to a variety of applications and could be composed of one or more of a variety of materials having a specified level of permeability. For example, the magnetic shims could include mu-metal, iron, steel, metglas, Permalloy, ferrite, or other materials. In some embodiments, one of the one or more magnetic shims could be disposed on a side of a magnetic segment opposite the target environment and configured to reduce the amount of magnetic flux produced by the magnetic assembly/segment in a direction opposite the target environment and/or to increase the amount of magnetic flux produced by the magnetic assembly/segment in the target environment. In some embodiments, one of the one or more magnetic shims could be a focusing pole configured to focus flux produced from one or more faces and/or magnetic elements of the magnetic assembly/segment toward the target environment. For example, the focusing pole could have a trapezoidal prism, triangular prism, conical, truncated conical, pyramidal, truncated pyramidal, or other narrowing geometry such that the focusing pole had a first cross-sectional area in contact with elements of the magnetic assembly/segment and a second, smaller cross-sectional area proximate to the target environment. In some embodiments, magnetic shims could be disposed between magnetic segments of the magnetic assembly (e.g., as spacers). Additionally or alternatively, spacers having a very low specified permeability could be disposed between magnetic segments of the magnetic assembly.

In some examples, the magnetic assembly could wholly or partially enclose the target environment. For example, the target environment could be a portion of vasculature in a wrist of a human, and the magnetic assembly could be configured to partially wrap around the wrist of the human. Correspondingly, magnetic segments of the magnetic assembly could be configured to wholly or partially enclose the target environment and could include one or a plurality of magnetic elements and/or magnetic shim elements arranged around the target environment according to a variety of configurations.

Magnetic assemblies as described herein (and devices including such magnetic assemblies) could be configured to provide a number of different applications related to magnetic particles (or other magnetic materials) in a target environment. In some examples, these applications are enabled by the magnetic particles being configured to bind to one or more analytes of interest. For example, the one or more analytes could be any analytes that, when present in or absent from the blood of a human, or present at a particular concentration or range of concentrations, may be indicative of a medical condition or health of the human. The one or more analytes could include enzymes, hormones, proteins, cells or other substances. In some examples, the applications are enabled by the magnetic particles, or chemicals, enzymes, or other moieties attached and/or bound to the magnetic particles, being configured to cause some chemical or biological effect in the target environment. For example, the magnetic particles could be attached to a pharmaceutical.

Applications of magnetic assemblies configured to exert forces on magnetic particles configured to selectively interact with one or more analytes could include detecting, measuring, and/or altering one or more properties of the one or more analytes. For example, the magnetic assembly could be configured to exert an attractive magnetic force on the magnetic particles such that the magnetic particles collected in the target environment (e.g., a portion of subsurface vasculature) proximate to a detector or other component configured to detect, measure, and/or alter one or more properties of the one or more analytes. In some examples, the one or more analytes could have a low concentration, such that a signal-to-noise ratio of a measurement of the one or more properties of the one or more analytes is increased due to the collection of the magnetic particles proximate to the detector. In some examples, an energy emitter could be configured to emit an energy sufficient to destroy, denature, or otherwise alter one or more properties of the one or more analytes. Collection proximate to the energy emitter of the one or more analytes bound to the magnetic particles can enable the energy emitter to effect a specified level or degree of alteration of the one or more analytes. Additionally or alternatively, the magnetic assembly could be configured to partition the magnetic particles based on whether individual magnetic particles are bound to the one or more analytes (or according to some other property), and the detection, measurement, and/or alteration of the analyte could be related to the partitioning of the magnetic particles based on binding to the one or more analytes. Other applications and configurations are anticipated.

The magnetic assembly could be configured to affect a rate of reaction, rate of activity, or other rate of modification of the one or more analytes. In some examples, an analyte (e.g., a pharmaceutical) could be removed from the target environment (e.g., by ultrafiltration through kidneys operatively coupled to a portion of subsurface vasculature) at a first rate in the absence of the magnetic particles and/or magnetic assembly. The introduction to the target environment of the magnetic particles configured to selectively bind to the one or more analytes, and the presence of the magnetic assembly configured to attract the magnetic particles proximate to the target environment, could result in the analyte being removed from the target at a second rate that is lower than the first rate. Further, one or more properties of the magnetic assembly (e.g., the proximity of the magnetic assembly to the target environment, a distance between one or more magnetic segments of the magnetic assembly, the direction of the magnetic moment(s) of one or more magnetic elements of the magnetic assembly) could be controlled to control the rate at which the analyte is removed from the target environment.

It should be understood that the above embodiments, and other embodiments described herein, are provided for explanatory purposes, and are not intended to be limiting. Further, the term 'parallel' is used herein (unless otherwise specified) to describe the relationship between two directions (e.g., vectors, axes, orientations) that are in substantially the same direction or that are in substantially opposite directions. The term 'antiparallel' is used herein (unless otherwise specified) to describe the relationship between two directions (e.g., vectors, axes, orientations) that are in substantially opposite directions.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. Illustrative Segmented Magnetic Assemblies

A magnetic assembly could include a plurality of magnetic segments (i.e., could be a 'segmented magnetic assembly'). This could include the magnetic assembly being composed of a plurality of discrete magnetic sub-assemblies (the magnetic segments) disposed within the magnetic assembly, with neighboring magnetic segments separated by respective distances. By segmenting (i.e., partitioning and separating by the specified distances) the magnetic-flux-producing elements (e.g., permanent magnets, electromagnets) of a magnetic assembly, a magnitude of a magnetic field and/or a magnetic field gradient produced by the magnetic assembly could be increased by introducing edge and/or fringe field effects at the edges of the magnetic segments (e.g., in the spaces between the magnetic segments).

Individual magnetic segments of such a segmented magnetic assembly could include one or more magnetic elements (i.e., magnetic-flux-producing elements) or other elements (e.g., magnetic shims, spacers, actuators) arranged in, e.g., a linear array. That is, the segments could be disposed along a long axis of the linear array. Individual magnetic segments of such an array could be regularly spaced (i.e., the specified distances between neighboring magnetic segments of magnetic assembly could be substantially identical) or could be spaced in some other way. Further, spacers or other elements could be disposed between the magnetic segments to align the segments, to control the distances between the magnetic segments (e.g., a thickness of a spacer could correspond to the specified distance between two neighboring magnetic segments), to alter a pattern of the magnetic field produced by the magnetic assembly (e.g., by being composed of material having a specified low magnetic permeability), or according to some other application.

Magnetic segments of a magnetic assembly could be configured in a variety of ways, as described herein or otherwise. Magnetic segments could be repeated (i.e., the configuration of two or more magnetic segments could be substantially the same), could be individual, or some combination thereof. For example, a magnetic assembly could include a linear array of magnetic segments including a first set of magnetic segments having a first configuration alternating in the array with a second set of magnetic segments having a second configuration. The first configuration and second configuration could be equivalent except for magnetic moments of corresponding magnetic elements being antiparallel. That is, magnetic moments of respective first and second magnetic elements of the first magnetic segment configuration are each oriented antiparallel to the magnetic moments of respective corresponding first and second magnetic elements of the second magnetic segment configuration. Other patterns of configuration of magnetic segments in a magnetic assembly are anticipated.

FIG. 1A illustrates first 110a and second 110b example magnetic segments. The magnetic segments 110a, 110b include three magnetic elements each (115a, 117a, 119a and 115b, 117b, 119b, respectively) having respective magnetic moments (arrows). The magnetic segments 110a, 110b additionally include respective enclosing magnetic shims 125a, 125b composed of a material having a specified high magnetic permeability. As illustrated, the sets of three magnetic elements 115a, 117a, 119a; 115b, 117b, 119b of the respective magnetic segments 110a, 110b are arranged as Halbach arrays. The example magnetic segments 110a, 110b are substantially planar.

Figure 1B:
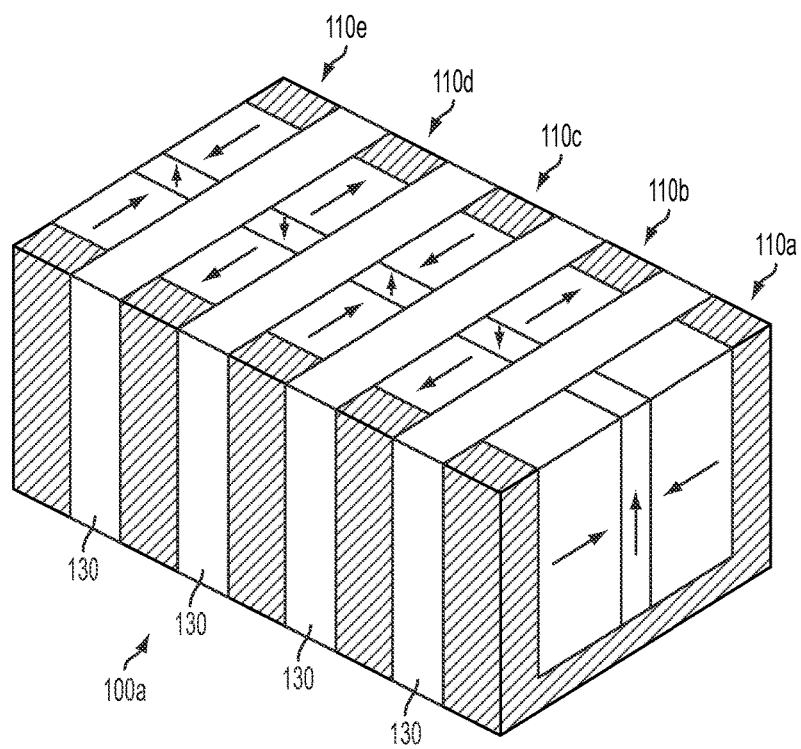
FIG. 1B is a perspective view of a magnetic assembly composed of a plurality of magnetic segments including the example magnetic segments illustrated in FIG. 1A.

FIG. 1B illustrates a magnetic assembly 100a that includes the first 110a and second 110b magnetic segments arranged in a linear array with additional magnetic segments 110c, 110d, 110e. The magnetic segments 110a, 110b, 110c, 110d, 110e are separated by respective spacers 130. The first 110a and second 110b magnetic segments, as arranged in the magnetic assembly 100a, are neighboring. Magnetic segments 110c and 110e are configured substantially identically to the first example segment 110a (i.e., 110a, 110c, and 110e are repeated segments); similarly, magnetic segment 110d is configured substantially identically to the second example segment 110b.

In this example, the first 110a and second 110b magnetic segments have certain similarities. In particular, the shape, size, composition, and relative location within the magnetic segment of elements of the first magnetic segment 110a correspond to the shape, size, composition, and relative location within the magnetic segment of corresponding elements of the second magnetic segment 110b (e.g., the shape, size, composition, and relative location within the first magnetic segment 110a of magnetic element 115a corresponds to the shape, size, composition, and relative location within the second magnetic segment 110b of magnetic element 115b). The first 110a and second 110b magnetic segments differ in that magnetic moments of corresponding magnetic elements of the first 110a and second 110b magnetic segments are antiparallel. That is, magnetic moments of respective first and second magnetic elements (e.g., 115a and 117a) of the first magnetic segment 110a are each oriented antiparallel to the magnetic moments of respective corresponding first and second magnetic elements (e.g., 115b and 117b) of the second magnetic segment 110b. Thus, magnetic segments of the magnetic assembly 100a could be described as being repeated with alternating moments.

The FIG. 1B example of magnetic assembly 100a being composed of substantially similar, repeated magnetic segments having alternating moments is intended as a non-limiting example. Magnetic segments of magnetic assemblies as described herein could have a variety of configurations (e.g., could have unique, non-repeated configurations within a given magnetic assembly) according to an application. For example, one or more properties of magnetic segments of a magnetic assembly (e.g., a segment thickness, a segment width, a segment magnetic element strength) could vary from one end of the linear array of the magnetic assembly to the other end of the linear array.

Further, the spacers 130 of the magnetic assembly 100a are illustrated as having substantially the same thickness. The location and/or spacing of magnetic segments of a magnetic assembly could be achieved by disposing the magnetic segments in a housing, by disposing spacers (e.g., 130) between the magnetic segments, by using an adhesive, or according to some other method(s). Spacers disposed between magnetic segments could have a variety of shapes, sizes (e.g., thicknesses corresponding to the specified distances between magnetic segments), and compositions. In some embodiments, such spacers could be composed of a material having a specified low magnetic permeability (e.g., aluminum, a polymer, an organic material or chemical). Alternatively, such spacers could be composed of a material having a specified high magnetic permeability (e.g., mu-metal, metglas, etc.). In some examples, first spacers of a magnetic assembly could have a first configuration (e.g., composition, thickness) and second spacers of the magnetic assembly could have a second configuration. Other configurations of spacers, magnetic segments, and/or other components of a magnetic assembly are anticipated.

Further, the example magnetic assembly 100a illustrates a straight linear array of magnetic segments, where the magnetic segments have straight, perpendicular faces (i.e., the magnetic segments take the shape of thin rectangular prisms), as an illustrative, non-limiting example. Additionally or alternatively, magnetic segments of a magnetic assembly could be arranged in curved or straight linear array (e.g., substantially planar magnetic segments, or otherwise configured magnetic segments, could be stacked and/or repeated along a long axis of the linear array), a branched array, a two- or three-dimensional array (e.g., repeated magnetic segments could be disposed across all or part of a surface of a sphere or other three-dimensional shape), or according to some other configuration.

In some examples, the magnetic assembly could wholly or partially enclose the target environment. For example, the target environment could be a portion of vasculature in a wrist of a human, and the magnetic assembly could be configured to partially wrap around the wrist of the human. Correspondingly, magnetic segments of the magnetic assembly could be configured to wholly or partially enclose the target environment and could include one or a plurality of magnetic elements and/or magnetic shim elements arranged around the target environment according to a variety of configurations.

Figure 2A:
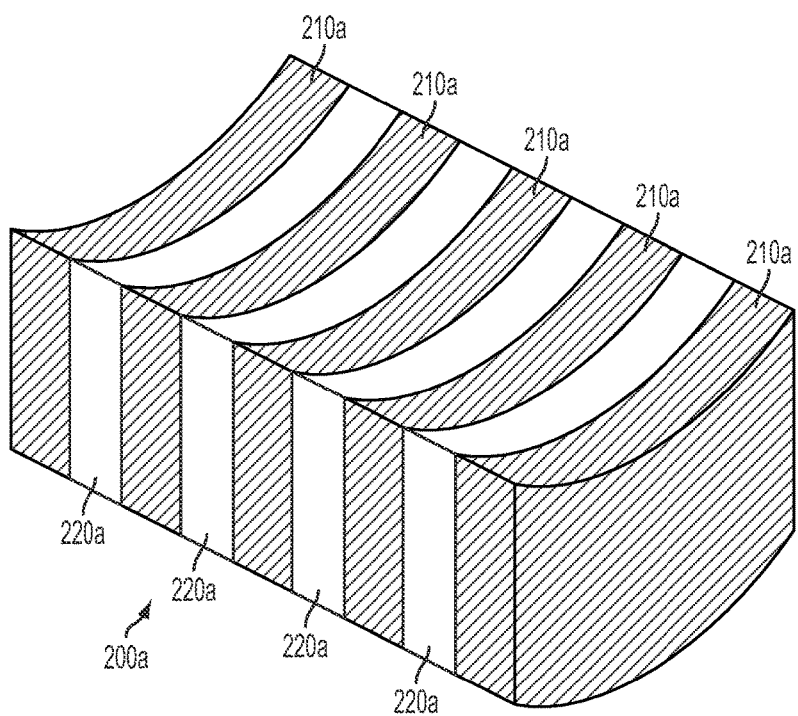
FIG. 2A is a perspective view of a magnetic assembly composed of a plurality of magnetic segments.
Figure 2B:
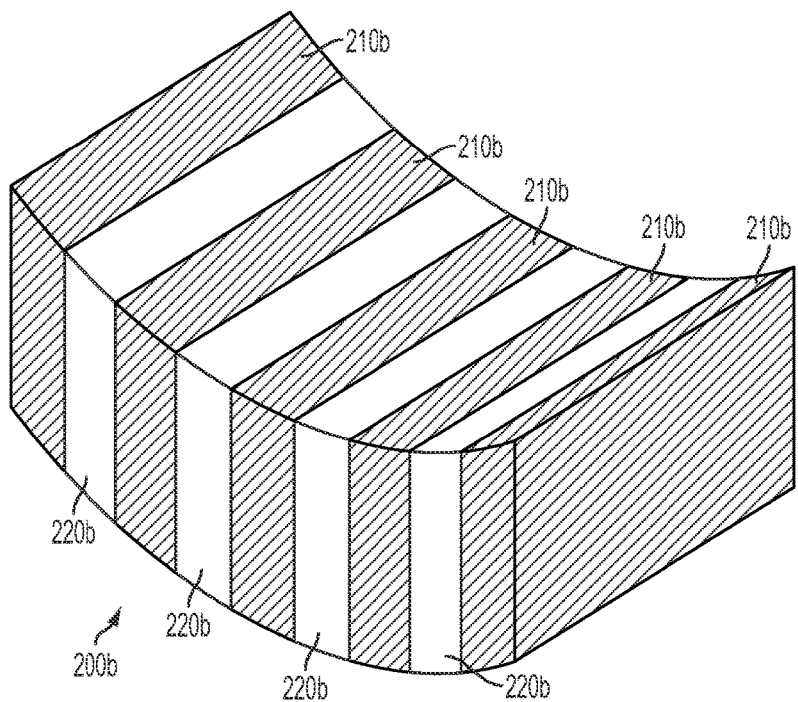
FIG. 2B is a perspective view of a magnetic assembly composed of a plurality of magnetic segments.

In some examples, this could include the magnetic segments being individually configured to wholly or partially enclose a target environment. FIG. 2A illustrates an example magnetic assembly 200a comprising a plurality of magnetic segments 210a arranged in a linear array and separated by respective specified distances by a plurality of spacers 220a. Individual magnetic segments 210a have a curved shape such that the magnetic assembly 200a is configured to partially enclose a target environment (e.g., a wrist of a human). Additionally or alternatively, the disposition of magnetic segments and/or other elements of a magnetic assembly within the magnetic assembly could be specified such that the magnetic assembly can wholly or partially enclose a target environment. FIG. 2B illustrates an example magnetic assembly 200b comprising a plurality of magnetic segments 210b arranged in a curved linear array and separated by respective specified distances by a plurality of spacers 220b. Individual magnetic segments 210b have a substantially flat, rectangular shape and are arranged along a curved surface such that the magnetic assembly 200a is configured to partially enclose a target environment (e.g., a wrist of a human). A magnetic assembly and components thereof (e.g., magnetic segments) could be configured in other ways to enclose and/or conform to other surfaces (e.g., to curve in multiple directions, to conform to the shape of a body part of a particular human) according to an application.

Figure 2C:
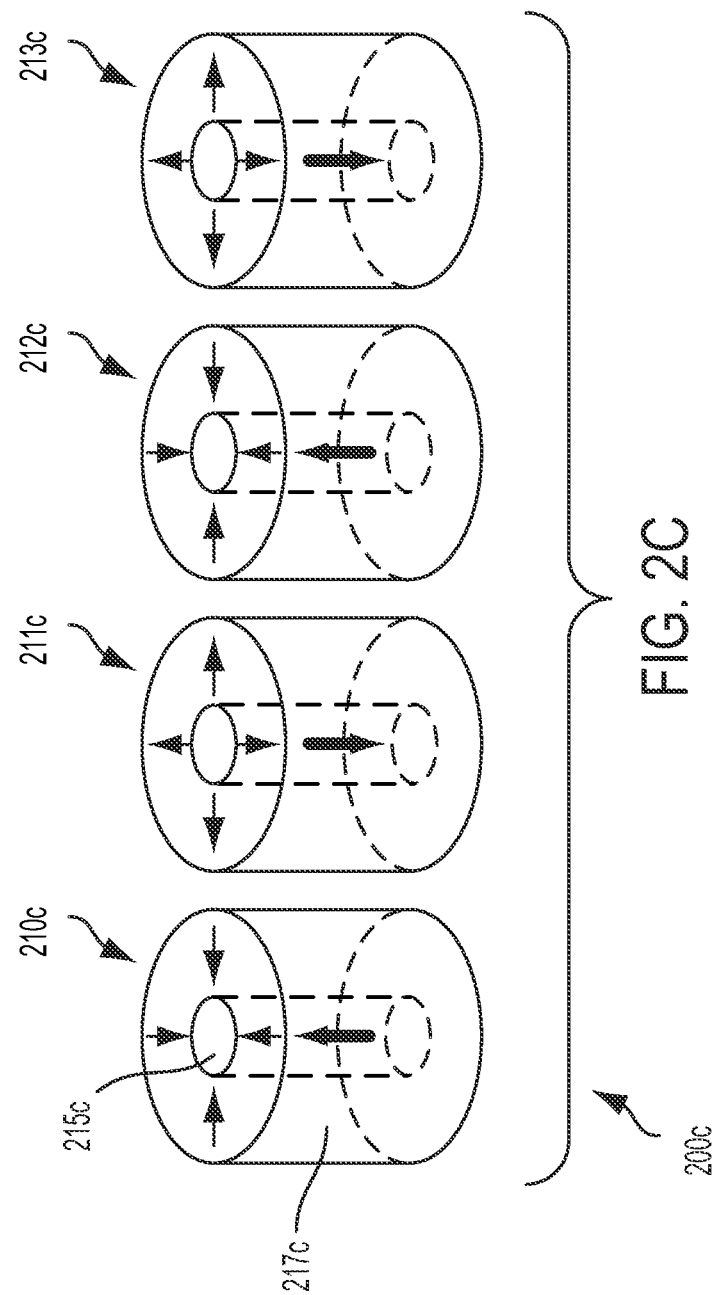
FIG. 2C is a perspective view of a magnetic assembly composed of a plurality of magnetic segments.

Further, magnetic segments of a segmented magnetic assembly need not be substantially flat and/or to have a substantially planar configuration. In some embodiments, a magnetic segment could have magnetic elements (and magnetic moments thereof) configured according to a cylindrical, a spherical, an ellipsoidal, or some other three-dimensional geometry configured to produce a magnetic flux and/or to cause a magnetic field produced by the magnetic segment to have a specified profile (i.e., a specified pattern of field magnitude, field direction, field gradient magnitude, field gradient direction) in one or more regions relative to the magnetic segment. FIG. 2C illustrates an example magnetic assembly 200c comprising a plurality of magnetic segments 210c, 211c, 212c, 213c arranged in a linear array and separated by respective specified distances. Individual magnetic segments 210c, 211c, 212c, 213c have a cylindrical geometry. Specifically, individual magnetic segments include an axial magnetic element (e.g., 215c) having a magnetic moment along a central axis of the axial magnetic element (thick-tailed arrows) and a plurality of radial magnetic elements (arranged as a ring around the axial magnetic moment, e.g., 217c) having respective magnetic moments (arrows) oriented toward the central axis of the axial magnetic element.

In this example, the magnetic segments 210c, 211c, 212c, 213c have certain similarities. In particular, the shape, size, composition, and relative location within the magnetic segment of elements of the first magnetic segment 210c (e.g., the axial 215c and radial 217c magnetic elements of the first magnetic segment 210c) correspond to the shape, size, composition, and relative location within the magnetic segment of corresponding elements of the other magnetic segments (e.g., the shape, size, composition, and relative location within the second magnetic segment 211c of the axial and radial magnetic elements of the second magnetic segment 211c correspond to the shape, size, composition, and relative location within the first magnetic segment 210c of the axial 215c and radial 217c magnetic elements of the first magnetic segment 210c). The first 210c and second 211c magnetic segments differ in that magnetic moments of corresponding magnetic elements and/or sub-section of magnetic elements of the first 210c and second 211c magnetic segments are antiparallel. That is, the magnetic moment of the axial magnetic element (e.g., 215c) of the first magnetic segment 210c oriented antiparallel to the magnetic moment of the corresponding axial magnetic element of the second magnetic segment 211c. Thus, magnetic segments of the magnetic assembly 200c could be described as being repeated with alternating moments.

Such magnetic elements could have curved external geometries (e.g., cylindrical external geometries, as illustrated in FIG. 2C) or could have other geometries, e.g., the segments could be flattened to allow for denser packing of individual magnetic segments into a linear array. Other external geometries, number and configuration of magnetic or other elements, or other properties of the configuration of such magnetic segments are anticipated.

III. Illustrative Magnetic Particles

In some examples, magnetic assemblies (and devices incorporating such magnetic assemblies) as described herein exert magnetic forces on magnetic particles disposed in a fluid environment. The fluid environment could include artificial environments (e.g., a fluid of an industrial process, a fluid of a chemical or pharmaceutical process) and natural environments (e.g., a lake, a river, a march, blood in vasculature of an animal). For example, the magnetic particles could be disposed in blood in a portion of subsurface vasculature of a human. The magnetic particles could be permanently magnetized (e.g., could be ferromagnetic) or could become magnetized when exposed to a magnetic field (e.g., could be paramagnetic) or to some other factor. A magnetic assembly exerting a magnetic force on such magnetic particles could include providing a magnetic field in the environment of the magnetic particles having a high magnitude of magnetic field gradient, such that permanent and/or induced magnetic moments of the magnetic particles are attracted in the direction of the gradient. A magnetic assembly exerting a magnetic force on such magnetic particles could additionally or alternatively include providing a magnetic field in the environment of the magnetic particles having a high magnitude, such that magnetic moments are induced in the magnetic particles and/or permanent and/or induced magnetic moments of the magnetic particles experience a torque aligning the magnetic moments with the direction of the magnetic field.

Generally, the magnitude of a magnetic force exerted on a magnetic particle is related to the magnitude of the permanent and/or induced magnetic dipole moment of the magnetic particle. In some examples, the magnitude of the permanent and/or induced magnetic dipole moment can be related to the mass and/or volume of magnetic material included in the magnetic particle. For example, the magnitude of the induced magnetic dipole moment of a magnetic particle that includes a particle of superparamagnetic iron oxide could be related to the volume of the particle of superparamagnetic iron oxide. The magnetic particles could be artificial (e.g., functionalized polystyrene shells containing and/or coating particles of superparamagnetic iron oxide), natural (e.g., particles of magnetite encapsulated in lipid bilayers in a cell), or could contain natural and artificial elements (e.g., an artificial magnetic particle onto which a variety of natural antibodies are adsorbed or otherwise attached).

Generally, the magnetic particles may be made of and/or wholly or partially coated by an inert material, such as polystyrene, and can have a diameter that is less than about 20 micrometers. In some embodiments, the magnetic particles have a diameter on the order of about 10 nm to 1 µm. In further embodiments, small particles on the order of 10-100 nm in diameter may be assembled to form a larger "clusters" or "assemblies" on the order of 1-10 micrometers. Those of skill in the art will understand a "particle" in its broadest sense and that it may take the form of any fabricated material, a molecule, tryptophan, a virus, a phage, etc. Further, a magnetic particle may be of any shape, for example, spheres, rods, non-symmetrical shapes, etc. In some examples, a magnetic material of the magnetic particles can include a paramagnetic, super-paramagnetic or ferromagnetic material or any other material that responds to a magnetic field. In some examples, the magnetic particles can include a magnetic moiety. Further, the particles can be configured to selectively bind to one or more analytes (e.g., chemicals, hormones, peptides, DNA or RNA fragments, cells). In some examples, the magnetic particles could be considered to include other elements (e.g., analytes, other magnetic or non-magnetic particles) bound to the magnetic particles. For example, a 'first magnetic particle' could include a particle of magnetic material functionalized to selectively interact with an analyte, and a 'second magnetic particle' could include one or more of the 'first magnetic particles' bound to the analyte, such that the 'second magnetic particle' is a composite particle including at least one instance of the analyte. Other embodiments of magnetic particles are anticipated.

In some examples, the magnetic particles are functionalized to selectively interact with an analyte of interest. The magnetic particles can be functionalized by covalently attaching a bioreceptor designed to selectively bind or otherwise recognize a particular analyte (e.g., a clinically-relevant analyte, e.g., a cancer cell). For example, magnetic particles may be functionalized with a variety of bioreceptors, including antibodies, nucleic acids (DNA, siRNA), low molecular weight ligands (folic acid, thiamine, dimercaptosuccinic acid), peptides (RGD, LHRD, antigenic peptides, internalization peptides), proteins (BSA, transferrin, antibodies, lectins, cytokines, fibrinogen, thrombin), polysaccharides (hyaluronic acid, chitosan, dextran, oligosaccharides, heparin), polyunsaturated fatty acids (palmitic acid, phospholipids), or plasmids. The functionalized magnetic particles can be introduced into a portion of subsurface vasculature of a person by injection, ingestion, inhalation, transdermal application, or in some other manner.

A clinically-relevant analyte could be any substance that, when present in the blood of a person or animal, or present at a particular concentration or range of concentrations, may directly or indirectly cause an adverse medical condition. For example, the clinically-relevant analyte could be an enzyme, hormone, protein, other molecule, or even whole or partial cells. In one relevant example, certain proteins have been implicated as a partial cause of Parkinson's disease. Thus, the development of Parkinson's disease might be prevented or retarded by providing magnetic particles functionalized with a bioreceptor that will selectively bind to this target. A magnetic force may then be exerted on these bound magnetic particles, using one or more magnetic assemblies as described herein (e.g., a magnetic assembly in a device positioned proximate to an external body surface that is proximate to a portion of subsurface vasculature), to collect, separate, detect, modify, or otherwise interact with the bound protein. As a further example, the analyte could be a cancer cell. By selectively collecting and then detecting, extracting (e.g., by use of an intravenous syringe), modifying, or destroying individual cancer cells (e.g., by emitting energy toward the magnetic particles such that the magnetic particles are heated sufficiently to cause an increase in temperature of the proximate bound cancer cells) the spread of cancer may be diminished and/or quantified.

Magnetic particles and/or magnetic assemblies (e.g., magnetic assemblies including a plurality of magnetic segments) configured to exert magnetic forces on such magnetic particles (and devices including such magnetic assemblies) could be configured and/or operated to provide a number of different applications. Applications could include detecting one or more properties of the magnetic particles, one or more properties of an analyte bound to or otherwise selectively interacting with the magnetic particles, collecting and/or extracting the magnetic particles and/or analytes bound to the magnetic particles, modifying and/or destroying the magnetic particles and/or analytes bound to the magnetic particles, or other applications.

A magnetic assembly exerting a force on magnetic particles could include exerting an attractive magnetic force on the magnetic particles. That is, the magnetic assembly could be configured to attract the magnetic particles toward the magnetic assembly. In some examples, the magnetic assembly could be configured to exert an attractive magnetic force of sufficient magnitude to collect the magnetic particles proximate to the magnetic assembly. For example, the magnetic particles could be disposed in blood of a wearer of a wearable device that includes the magnetic assembly, and the wearable device including the magnetic assembly could be mounted to an external body surface of the wearer proximate to the portion of subsurface vasculature such that the magnetic particles collect in the portion of subsurface vasculature proximate to the magnetic assembly. Additionally or alternatively, the magnetic assembly could be disposed in a desktop device, in a device mounted and/or installed in a floor, wall, or ceiling of a room, or in some other device and the device and/or a portion of the body of the wearer could be positioned such that the magnetic particles collect in the portion of subsurface vasculature proximate to the magnetic assembly.

FIG. 3A is a partial cross-sectional side view of a human wrist illustrating the operation of an example wrist-mounted device. In the example shown in FIG. 3A, the wrist-mounted device 300a includes a magnetic assembly 370a mounted on a strap or wrist-band 320a and oriented on the posterior side 395a of the wearer's wrist. Magnetic particles 340a have been introduced into a lumen of subsurface vasculature 330a of the human by one of the means discussed herein. Magnetic assembly 370a generates a magnetic field 372a that exerts a magnetic force sufficient to cause magnetic particles 340a present in a lumen of the subsurface vasculature 330a to collect in a region proximal to the magnetic assembly 370a. Magnetic assembly 370a is composed of a plurality of magnetic segments separated by spacers, as described elsewhere herein.

The forces exerted by magnetic assemblies as described herein could be attractive (i.e., toward the magnetic assembly) or could be directed in other directions. For example, the magnetic forces exerted by the magnetic assembly could be directed away from the magnetic assembly, in a direction parallel to a flow of fluid in which the magnetic particles are disposed (e.g., in the direction of or against the direction of blood flowing in a portion of subsurface vasculature), or in some other direction according to an application. Generally, the magnitude of the magnetic force exerted on a magnetic particle can be related to the volume of the magnetic particle (i.e., to an amount of magnetic material in the particle) while the magnitude of fluid forces (e.g., drag, convective forces) on a magnetic particle can be related to a surface area and/or effective cross-sectional area of the magnetic particle.

As such, first magnetic particles can experience a first magnetic force (and/or ratio of magnetic to fluid force) such that the first magnetic particles are separated from, differentially collected relative to, or otherwise differently affected by the magnetic assembly relative to second magnetic particles. The second magnetic particles have different properties (e.g., size, degree of aggregation, binding state) relative to the first magnetic particles and experience a second magnetic force (and/or ratio of magnetic to fluid force) that is different from the first magnetic force and/or ratio of magnetic to fluid force. Separation, differential collection, or other differential effects of two or more groups of magnetic particles could be dependent on one or more properties of an environment containing the two or more groups of magnetic particles, e.g., a flow rate and/or flow profile or fluid in the containing environment. For example, separation and collection of two or more groups of magnetic particles in a portion of subsurface vasculature could be related to a flow rate of blood in the portion of subsurface vasculature.

In some examples, magnetic forces could be exerted on more than one type of magnetic particles in an environment. The magnetic forces could be different according to the type of magnetic particles and could be related to corresponding different properties of the types of magnetic particles. The different types of magnetic particles could be collected at respective different locations in an environment (e.g., a lumen of subsurface vasculature) and/or could be collected or otherwise differentially manipulated by a magnetic assembly to enable a variety of applications. For example, a separation distance between magnetic segments of a magnetic assembly could have a first value for a first set of magnetic segments and a second value for a second set of magnetic segments such that first magnetic particles are collected proximate to the first set of magnetic segments and such that second magnetic particles are collected proximate to the second set of magnetic segments. Additionally or alternatively, first and second sets of magnetic segments of a magnetic assembly could have respective first and second configurations (e.g., number, size, shape, composition, relative location, or other properties of elements of the magnetic segments) that are different and that result in corresponding first and second magnetic particles being collected proximate to the first and second sets of magnetic segments, respectively.

FIG. 3B is a partial cross-sectional side view of a human wrist illustrating the operation of an example wrist-mounted device. In the example shown in FIG. 3B, the wrist-mounted device 300b includes a magnetic assembly 370b mounted on a strap or wrist-band 320b and oriented on the posterior side 395b of the wearer's wrist. First magnetic particles 340b and second magnetic particles 350b have been introduced into a lumen of subsurface vasculature 330b of the human by one of the means discussed herein. Magnetic assembly 370b includes first 373b and second 375b sets of magnetic segments having respective specified first and second inter-segment distances (e.g., relating to respective sets of spacers having respective specified thicknesses). The magnetic assembly 370b generates a magnetic field 372b that exerts a magnetic force sufficient to collect first 340b and second 350b magnetic particles in respective regions proximate to the first 373b and second 375b sets of magnetic segments, respectively, of the magnetic assembly 370b. This collection in separate regions could be related to the magnetic assembly 370b exerting a greater attractive force on the first magnetic particles 340b, the first magnetic particles 340b being subject to less drag or other fluid forces, the magnetic assembly 370b exerting forces on the first 340b and second 350b magnetic particles parallel to the direction of flow in the lumen of subsurface vasculature 330b, or could be related to additional or alternative factors.

In some examples, more than two types of magnetic particles could be attracted to respective more than two locations relative to respective more than two sets of magnetic segments of the magnetic assembly 370b. In some examples, magnetic particles could have a range of properties related to a range of collection locations relative to the magnetic assembly 370b (e.g., the magnetic particles could be arranged topographically relative to a property of the magnetic particles, e.g., the magnetic particles could be arranged from largest to smallest, or according to some other property or combination of properties).

In some examples, a magnetic assembly could exert magnetic forces on magnetic particles in an environment without collecting the magnetic particles. For example, a magnetic assembly could generate a magnetic field that exerts a magnetic force sufficient to separate first and second magnetic particles present in a lumen of subsurface vasculature and proximate to the magnetic assembly. This separation could be related to the first magnetic particles being subject to less drag or other fluid forces, the magnetic assembly exerting forces on the first and second magnetic particles parallel to the direction of flow in the lumen of subsurface vasculature, or could be related to additional or alternative factors. In some examples, more than two types of magnetic particles could be separated in a direction/region relative to the magnetic assembly. In some examples, magnetic particles could have a range of properties related to a range separation magnitudes/regions relative to the magnetic assembly (e.g., the magnetic particles could be slowed/sped in a flow to a degree relative to a property of the magnetic particles, e.g., the largest magnetic particles could be slowed the most while the smallest magnetic particles could be slowed the least, or according to some other property or combination of properties).

Other manipulations and/or magnetic forces could be applied to magnetic particles in an environment than those described above. The manipulations and/or magnetic forces could be related to properties of the magnetic particles (e.g., size, magnetic dipole moment, drag coefficient, cross-sectional area, degree of aggregation with other magnetic particles, whether the magnetic particles is bound to an analyte), properties of the environment containing the magnetic particles (e.g., a viscosity, a pH, a degree of polarity of a solvent, a flow rate, a flow profile, a degree of turbulence), or other factors. For example, magnetic particles could be collected or otherwise manipulated in a manner related to where in a flow the articles are located, e.g., magnetic particles in low-flow-rate regions could be collected while magnetic particles in high-flow regions could not be collected.

Magnetic assemblies, magnetic segments, devices containing magnetic assemblies and/or magnetic segments, magnetic particles, and other aspects and embodiments described herein could be configured and/or operated to provide a variety of applications. In some examples, magnetic particles could be configured to bind to an analyte of interest, and a magnetic assembly could be configured to collect or otherwise manipulate the magnetic particles to enable the detection, extraction, modification, or other manipulation of the analyte. For example, a detector could be disposed proximate to a magnetic assembly that is configured to collect the magnetic particles, and the detector could detect one or more properties of the analyte bound to the magnetic particles (e.g., by detecting an optical property of the analyte and/or magnetic particles (e.g., fluorescent detection of a fluorophore), by detecting a magnetic property of the magnetic particles). Additionally or alternatively, an energy emitter could be disposed proximate to the magnetic assembly, and the energy emitter could emit energy toward the collected magnetic particles sufficient to alter one or more properties of the analyte (e.g., to destroy, denature, heat, change a conformation state of, other otherwise modify the analyte). In some examples, collection of an analyte bound to magnetic particles by a magnetic assembly could enable the extraction of the analyte and magnetic particles (e.g., using a hypodermic needle).

In some applications, manipulation of magnetic particles could enable detection and/or modification of an analyte. For example, the reaction (e.g., a differential and/or absolute motion) of a magnetic particle to a magnetic field generated by a magnetic assembly could be detected, and one or more properties of the reaction could be used to determine one or more properties of the magnetic particle. For example, a change in velocity of a magnetic particle, when exposed to the magnetic field of the magnetic assembly, could be related to whether the magnetic particle was bound to an analyte. In some examples, the magnetic particles could be configured to couple an oscillating electromagnetic field into an increase in heat proximate to the magnetic particle, and this increase in heat could be used to detect one or more properties of the magnetic particle and/or to modify the environment proximate to the particle (e.g., to denature an analyte bound to the magnetic particle). Other configurations, operations, and applications of the embodiments described herein are anticipated.

The terms "binding", "bound", and related terms used herein are to be understood in their broadest sense to include any interaction between the receptor and the target or another functionalized particle such that the interaction allows the target to be modified or destroyed by energy emitted from a device.

IV. Example Magnetic Segments

In some applications, it can be desirable to produce magnetic fields having high magnitude, high magnitude of field gradient, a specified field profile, or other properties using a small device and using minimal power. For example, an application could include a wearable device configured to be powered by a battery disposed in the device and to attract magnetic particles in the body of a wearer of a device. Such magnetic fields could be produced by magnetic assemblies that include magnetic elements (i.e., permanent magnets, electromagnets, and other components that have and/or can be operated to have a magnetic dipole moment), paramagnetic materials, flux-focusing and/or shielding shims or poles, or other elements. A class of such magnetic elements includes unpowered elements, e.g., permanent magnets and other magnetic materials capable of generating a magnetic field having a desired profile, magnitude, or other property while requiring significantly no applied power.

Further, such magnetic assemblies could be composed of magnetic segments that are separated by respective specified distances. The configuration of a magnetic assembly in such a way could increase a magnitude of a magnetic field and/or a magnetic field gradient produced by a given mass, area, or other amount of magnetic material by introducing edge and/or fringe field effects at the edges of the magnetic segments (e.g., in the spaces between the magnetic segments). As a result, a magnetic assembly that includes a given mass of magnetic material configured as a linear array of magnetic segments (as described herein) could exert a greater attracted magnetic force (e.g., on magnetic particles in a portion of subsurface vasculature proximate to the magnetic assembly) than a magnetic assembly that includes a same mass of magnetic material that is not configured as a plurality of magnetic segments.

Magnetic segments of a magnetic assembly could be configured in a variety of ways, as described herein or otherwise. Magnetic segments could be repeated (i.e., the configuration of two or more magnetic segments could be substantially the same), could be individual, or some combination thereof. For example, a magnetic assembly could include a linear array of magnetic segments including a first set of magnetic segments having a first configuration alternating in the array with a second set of magnetic segments having a second configuration. The first configuration and second configuration could be equivalent except for magnetic moments of corresponding magnetic elements being antiparallel. That is, magnetic moments of respective first and second magnetic elements of the first magnetic segment configuration are each oriented antiparallel to the magnetic moments of respective corresponding first and second magnetic elements of the second magnetic segment configuration. Other patterns of configuration of magnetic segments in a magnetic assembly are anticipated.

Magnetic segments of a magnetic assembly could be arranged in curved or straight linear array (e.g., substantially planar magnetic segments could be stacked and/or repeated along a long axis of the linear array), a branched array, a two- or three-dimensional array (e.g., repeated magnetic segments could be disposed across all or part of a surface of a sphere or other three-dimensional shape), or according to some other configuration. Individual magnetic segments could be separated from neighboring magnetic segments by respective distances. Such distances could be substantially the same across an array of magnetic segments (e.g., the magnetic segments could be regularly spaced) or could vary according to an application. The location and/or spacing of the magnetic segments could be achieved by disposing the magnetic segments in a housing, by disposing spacers between the magnetic segments, by using an adhesive, or according to some other method(s). Spacers disposed between magnetic segments could have a variety of shapes, sizes (e.g., thicknesses corresponding to the specified distances between magnetic segments), and compositions. In some embodiments, such spacers could be composed of a material having a specified low magnetic permeability (e.g., aluminum, a polymer, an organic material or chemical). Alternatively, such spacers could be composed of a material having a specified high magnetic permeability (e.g., mu-metal, metglas, etc.). In some examples, first spacers of a magnetic assembly could have a first configuration (e.g., composition, thickness) and second spacers of the magnetic assembly could have a second configuration. Other configurations of spacers, magnetic segments, and/or other components of a magnetic assembly are anticipated.

Such magnetic segments could include one or more magnetic elements, with each magnetic element of the one or more magnetic elements having a respective magnetic moment that is oriented relative to an environment of interest (e.g., a portion of subsurface vasculature of a user of a device that includes the one or more magnetic elements) and/to elements of neighboring magnetic segments to enable some application (e.g., the exertion of a magnetic force to enable collection, separation, or some other manipulation of one or more magnetic particles in the portion of subsurface vasculature). The magnetic segment could include two or more magnetic elements arranged to provide a specified magnetic field in the environment proximate to the magnetic elements. For example, the magnetic segment could include a first magnetic element that can be operated to have a magnetic moment oriented toward a portion of subsurface vasculature, and a second magnetic element that can be operated to have a magnetic moment oriented away from the portion of subsurface vasculature, such that a region between the opposite poles of the first and second magnetic elements had a desired high magnitude of magnetic field gradient or some other specified property. Similarly, corresponding magnetic elements of neighboring magnetic segments (e.g., elements having similar size, shape, and relative location within respective magnetic segments) could have respective magnetic moments that are antiparallel. Magnetic segments could additionally or alternatively include magnetic shims or poles (e.g., materials having high magnetic permeability or some other specified magnetic property) configured to focus magnetic flux toward a specified region of an environment and/or shield a specified region of an environment from magnetic flux.

Figures 4A, 4B:
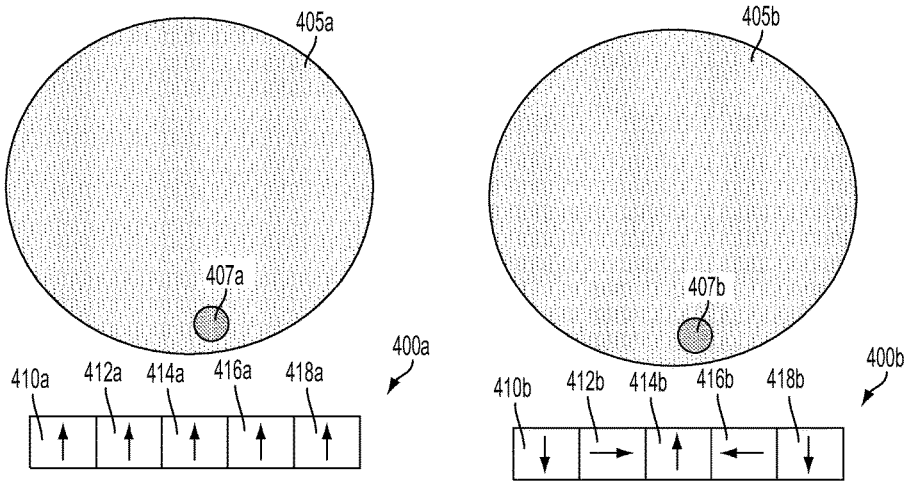
FIG. 4A is cross-sectional view of an example magnetic segment, while positioned near a lumen of subsurface vasculature.
FIG. 4B is cross-sectional view of an example magnetic segment, while positioned near a lumen of subsurface vasculature.

FIG. 4A illustrates a schematic diagram of an example magnetic segment 400a comprising a plurality of magnetic elements 410a, 412a, 414a, 416a, 418a having respective magnetic moments (arrows). The magnetic segment 400a is positioned proximate to a portion of subsurface vasculature 407a within a body of a human 405a. The magnetic segment 400a could be part of a wearable device (e.g., could be one of a set of magnetic segments of a magnetic assembly) and the wearable device could further include a mount configured to mount the wearable device to an external body surface of the body of the human 405a proximate to the portion of subsurface vasculature 407a. The permanent magnets 410a, 412a, 414a, 416a, 418a of the magnetic segment 400a can be configured to exert a magnetic force on magnetic particles in the portion of subsurface vasculature 407a.

Magnetic elements of a magnetic segment could have magnetic moments oriented in substantially the same direction (as illustrated in the example of FIG. 4A) or could have a number of orientations relative to each other, to magnetic elements of neighboring magnetic segments, and/or to an environment of interest. In some examples, the orientations of the magnetic moments could be specified to increase one or more properties of a generated magnetic field (e.g., a field magnitude, a magnitude of a field gradient) in a first region and/or to reduce one or more properties of the generated magnetic field in a second region. For example, the magnetic moments of three or more magnetic elements in a magnetic segment could be arranged as a Halbach array to increase the magnitude of the magnetic field on one side of a magnetic assembly that includes the magnetic segment (e.g., a side toward an environment of interest, e.g., toward a portion of subsurface vasculature) and to decrease the magnitude of the magnetic field on an opposite side of the magnetic assembly.

FIG. 4B illustrates a schematic diagram of an example magnetic segment 400b comprising a plurality of magnetic elements 410b, 412b, 414b, 416b, 418b having respective magnetic moments (arrows) oriented such that the magnetic segment forms a Halbach array. The magnetic segment 400b is positioned proximate to a portion of subsurface vasculature 407b within a body of a human 405b. The magnetic segment 400b could be part of a wearable device (e.g., could be one of a set of magnetic segments of a magnetic assembly) and the wearable device could further include a mount configured to mount the wearable device to an external body surface of the body of the human 405b proximate to the portion of subsurface vasculature 407b. The magnetic elements 410b, 412b, 414b, 416b, 418b of the magnetic segment 400b can be configured to exert a magnetic force on magnetic particles in the portion of subsurface vasculature 407b. The magnetic elements 410b, 412b, 414b, 416b, 418b being arranged as a Halbach array comprises the orientation of the magnetic moment of an individual magnetic element being substantially perpendicular to (i.e., rotated approximated ninety degrees relative to) the magnetic moments of magnetic elements in the array adjacent to the individual magnetic element and substantially antiparallel to (i.e., rotated approximated 180 degrees relative to) magnetic elements in the array that are adjacent to the magnetic elements that are adjacent to the individual magnetic element. Other arrangements of the magnetic moments of magnetic elements of a magnetic array relative to the magnetic elements of the magnetic segment, elements of neighboring magnetic segments, and/or an environment of interest proximate to the magnetic segment are anticipated.

In some examples, the magnetic segment (and a magnetic assembly containing such) could wholly or partially enclose an environment (e.g., an aspect of a body of a wearer, e.g., a wrist). That is, a magnetic segment, a magnetic assembly, and/or a wearable or other device including a magnetic segment could have a concave surface configured to at least partially enclose a corresponding convex surface of an environment of interest (e.g., the magnetic segment could have a concave surface configured to at least partially enclose a convex shape of an external body surface of a human or other target of the magnetic assembly). Further, one or more of a plurality of magnetic elements of the magnetic segment could be disposed on the concave surface.

Figures 4C, 4D:
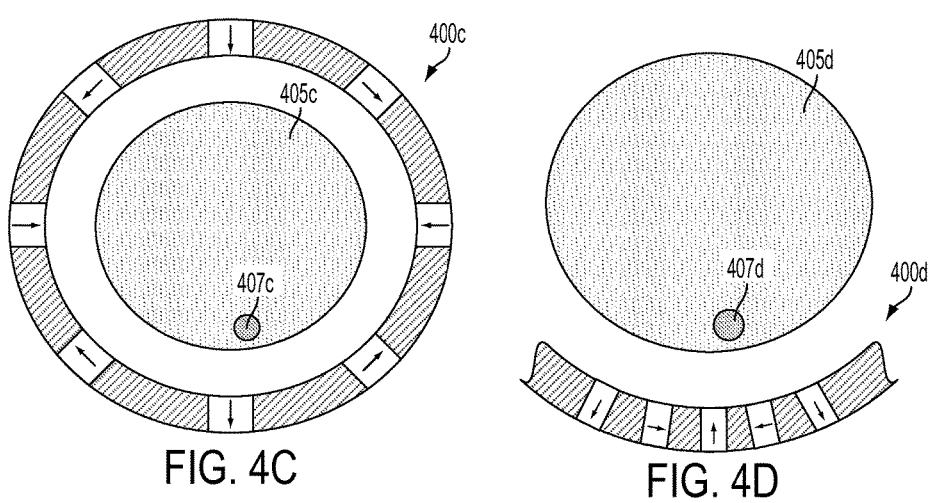
FIG. 4C is cross-sectional view of an example magnetic segment, while positioned near a lumen of subsurface vasculature.
FIG. 4D is cross-sectional view of an example magnetic segment, while positioned near a lumen of subsurface vasculature.

FIGS. 4C and 4D illustrate schematic diagrams of example magnetic segments 400c, 400d comprising respective pluralities of magnetic elements having respective magnetic moments (arrows) oriented such that the magnetic segments 400c, 400d form respective configurations of Halbach arrays. The magnetic segments 400c, 400d are positioned proximate to respective portions of subsurface vasculature 407c, 407d within respective bodies of respective humans 405c, 405d. The magnetic segments 400c could be part of respective wearable devices (e.g., could be one of a set of magnetic segments of a magnetic assembly) and the wearable devices could further include mounts configured to mount the wearable devices to respective external body surfaces of the bodies of the respective humans 405c, 405d proximate to the respective portions of subsurface vasculature 407c, 407d. The magnetic elements of the magnetic assemblies 400c, 400d can be configured to exert magnetic forces on magnetic particles in respective portions of subsurface vasculature 407c, 407d.

Magnetic assemblies and/or magnetic segments thereof can include magnetic poles (also called magnetic shims) configured to focus, block, or otherwise modify a pattern of magnetic flux and/or a magnetic field profile generated by one or more magnetic elements. The magnetic poles can have a variety of specified geometries and be composed of a variety of materials according to a variety of applications. The magnetic poles could be composed of materials having a specified magnetic property (e.g., permeability, reluctance, susceptibility, coercivity, remanence, saturation level). For example, the magnetic poles could be composed of one or more materials having a high magnetic permeability, e.g., mu-metal, iron, steel, metglas, Permalloy, ferrite, or other materials.

Figure 5A:
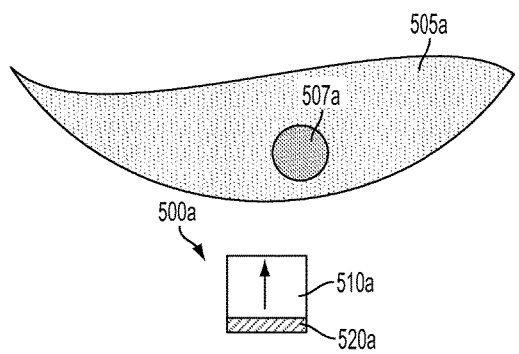
FIG. 5A is cross-sectional view of an example magnetic segment, while positioned near a lumen of subsurface vasculature.

FIG. 5A illustrates a schematic diagram of an example magnetic segment 500a comprising a magnetic element 510a having a magnetic moment (arrow) and a magnetic pole 520a comprising a high-permeability material. The magnetic segment 500a is positioned proximate to a portion of subsurface vasculature 507a within a body of a human 505a. The magnetic pole 520a comprises a layer of the high-permeability material disposed on a side of the magnetic segment 500a opposite the human body 505a. The magnetic segment 500a could be part of a wearable device (e.g., could be one of a set of magnetic segments of a magnetic assembly) and the wearable device could further include a mount configured to mount the wearable device to an external body surface of the body of the human 505a proximate to the portion of subsurface vasculature 507a. The magnetic element 510a and pole 520a of the magnetic segment 500a can be configured to exert a magnetic force on magnetic particles in the portion of subsurface vasculature 507a.

Further, the magnetic pole 520a could act to increase a property (e.g., a magnitude, a gradient magnitude) of the magnetic field produced by the magnetic segment 300a in the portion of subsurface vasculature 507a and to decrease a property (e.g., a magnitude, a gradient magnitude) of the magnetic field produced by the magnetic segment 500a in a region away from the body of the human 505a (i.e., to 'shield' the region below the magnetic segment 500a from the magnetic field produced by the magnetic element 510a). Further, the magnetic pole 520a could be associated specifically with the illustrated magnetic segment 500a or could extend past the magnetic segment 500a to associate with (e.g., to be in contact with) other magnetic segments of a magnetic assembly that includes the magnetic segment 500a.

Figure 5B:
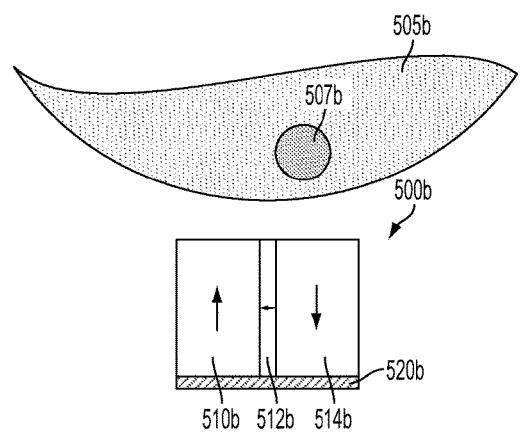
FIG. 5B is cross-sectional view of an example magnetic segment, while positioned near a lumen of subsurface vasculature.

FIG. 5B illustrates a schematic diagram of an example magnetic segment 500b comprising a plurality of magnetic elements 510b, 512b, 514b having respective magnetic moments (arrows) oriented such that the magnetic segment forms a Halbach array. The magnetic segment 500b additionally includes a magnetic pole 520a comprising a high-permeability material. The magnetic segment 500b is positioned proximate to a portion of subsurface vasculature 507b within a body of a human 505b. The magnetic pole 520b comprises a layer of the high-permeability material disposed on a side of the magnetic segment 500b opposite the human body 505b. The magnetic segment 500b could be part of a wearable device (e.g., could be one of a set of magnetic segments of a magnetic assembly) and the wearable device could further include a mount configured to mount the wearable device to an external body surface of the body of the human 505b proximate to the portion of subsurface vasculature 507b. The magnetic elements 510b, 512b, 514b of the magnetic segment 500b can be configured to exert a magnetic force on magnetic particles in the portion of subsurface vasculature 507b. The magnetic elements 510b, 512b, 514b being arranged as a Halbach array comprises the orientation of the magnetic moment of an individual magnetic element being substantially perpendicular to (i.e., rotated approximated ninety degrees relative to) the magnetic moments of magnetic elements in the array adjacent to the individual magnetic element and substantially antiparallel to (i.e., rotated approximated 180 degrees relative to) magnetic elements in the array that are adjacent to the magnetic elements that are adjacent to the individual magnetic element. Other arrangements of the magnetic moments of magnetic elements of a magnetic array relative to the magnetic elements of the magnetic segment, elements of neighboring magnetic segments, and/or an environment of interest proximate to the magnetic segment are anticipated.

Further, the magnetic pole 520b could act to increase a property (e.g., a magnitude, a gradient magnitude) of the magnetic field produced by the magnetic segment 500b in the portion of subsurface vasculature 507b and to decrease a property (e.g., a magnitude, a gradient magnitude) of the magnetic field produced by the magnetic segment 500b in a region away from the body of the human 505b (i.e., to 'shield' the region below the magnetic segment 500b from the magnetic field produced by the magnetic elements 510b, 512b, 514b). Further, the magnetic pole 520b could be associated specifically with the illustrated magnetic segment 500b or could extend past the magnetic segment 500b to associate with (e.g., to be in contact with) other magnetic segments of a magnetic assembly that includes the magnetic segment 500b.

Figure 5C:
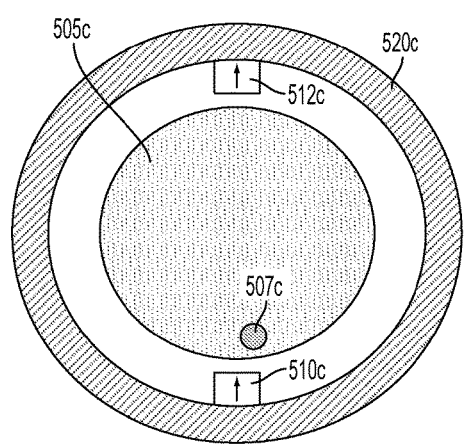
FIG. 5C is cross-sectional view of an example magnetic segment, while positioned near a lumen of subsurface vasculature.

In some examples, the magnetic poles and/or magnetic elements of the magnetic segment could wholly enclose an environment (e.g., a wrist or other body portion of a user). FIG. 5C illustrates a schematic diagram of an example magnetic segment 500c comprising a plurality of magnetic elements (510c, 512c) having respective magnetic moments (arrows). The magnetic segment 500c is positioned proximate to a portion of subsurface vasculature 507c within the body of a human 505c. The magnetic segment 500c could be part of a wearable device (e.g., could be one of a set of magnetic segments of a magnetic assembly) and the wearable device could further include a mount configured to mount the wearable device to an external body surface of the body of the human 505c proximate to the portion of subsurface vasculature 507c. The magnetic segment 500c wholly encloses a portion of the body of the human 507c with a magnetic pole 520c configured to transmit magnetic flux between the magnetic elements 510c, 512c to increase a property (e.g., a magnitude, a gradient magnitude) of the magnetic field produced by the magnetic segment 500c in the portion of subsurface vasculature 507c and to decrease a property (e.g., a magnitude, a gradient magnitude) of the magnetic field produced by the magnetic segment 500c outside of the enclosing magnetic pole 520c (i.e., to 'shield' the region outside of the enclosing magnetic pole 520c). Further, the magnetic pole 520c could be associated specifically with the illustrated magnetic segment 500c or could extend past the magnetic segment 500c to associate with (e.g., to be in contact with) other magnetic segments of a magnetic assembly that includes the magnetic segment 500c.

Figure 5D:
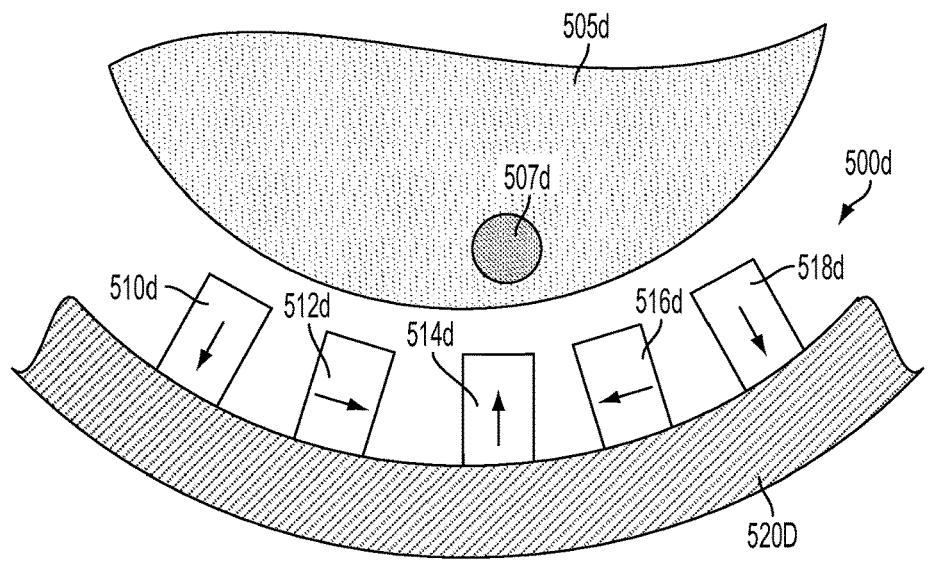
FIG. 5D is cross-sectional view of an example magnetic segment, while positioned near a lumen of subsurface vasculature.

In some examples, the magnetic poles and/or magnetic elements of the magnetic assembly (e.g., of a magnetic segment of the magnetic assembly) could partially enclose an environment (e.g., a wrist or other body portion of a user). FIG. 5D illustrates a schematic diagram of an example magnetic segment 500d comprising a plurality of magnetic elements (510d, 512d, 514d, 516d, 518d) having respective magnetic moments (arrows). The magnetic segment 500d is positioned proximate to a portion of subsurface vasculature 507d within a body of a human 505d. The magnetic segment 500d could be part of a wearable device (e.g., could be one of a set of magnetic segments of a magnetic assembly) and the wearable device could further include a mount configured to mount the wearable device to an external body surface of the body of the human 505d proximate to the portion of subsurface vasculature 507d. The magnetic segment 500d partially encloses a portion of the body of the human 507d with a magnetic pole 520d that is configured to increase a property (e.g., a magnitude, a gradient magnitude) of the magnetic field produced by the magnetic segment 500d in the portion of subsurface vasculature 507d and to decrease a property (e.g., a magnitude, a gradient magnitude) of the magnetic field produced by the magnetic segment 500d in a region away from the body of the human 505d (i.e., to 'shield' the region below the magnetic segment 500d from the magnetic field produced by the magnetic elements 510d, 512d, 514d, 516d, 518d). Further, the magnetic pole 520d could be associated specifically with the illustrated magnetic segment 500d or could extend past the magnetic segment 500d to associate with (e.g., to be in contact with) other magnetic segments of a magnetic assembly that includes the magnetic segment 500d.

Figure 5E:
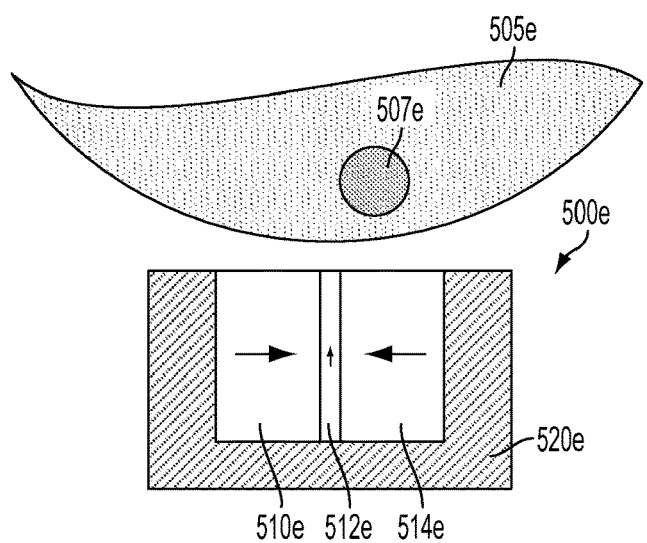
FIG. 5E is cross-sectional view of an example magnetic segment, while positioned near a lumen of subsurface vasculature.

FIG. 5E illustrates a schematic diagram of an example magnetic segment 500e comprising a plurality of magnetic elements 510e, 512e, 514e having respective magnetic moments (arrows) oriented such that the magnetic segment forms a Halbach array, and such that a middle magnetic element 512e has a magnetic moment oriented toward a portion of subsurface vasculature 507e within a body of a human 505e. The magnetic segment 500e additionally includes a magnetic pole 520e comprising a high-permeability material. The magnetic segment 500e is positioned proximate to the portion of subsurface vasculature 507e within the body of the human 505e. The magnetic pole 520e comprises a layer of the high-permeability material disposed on at least three sides of the magnetic segment 500e: opposite the human body 505e, opposite the left magnetic element 510e from the middle magnetic element 512e, and opposite the right magnetic element 514e from the middle magnetic element 512e. The magnetic segment 500e could be part of a wearable device (e.g., could be one of a set of magnetic segments of a magnetic assembly) and the wearable device could further include a mount configured to mount the wearable device to an external body surface of the body of the human 505e proximate to the portion of subsurface vasculature 507e. The magnetic elements 510e, 512e, 514e of the magnetic segment 500e can be configured to exert a magnetic force on magnetic particles in the portion of subsurface vasculature 507e.

The magnetic elements 510e, 512e, 514e being arranged as a Halbach array comprises the orientation of the magnetic moment of an individual magnetic element being substantially perpendicular to (i.e., rotated approximated ninety degrees relative to) the magnetic moments of magnetic elements in the array adjacent to the individual magnetic element and substantially antiparallel to (i.e., rotated approximated 180 degrees relative to) magnetic elements in the array that are adjacent to the magnetic elements that are adjacent to the individual magnetic element. Other arrangements of the magnetic moments of magnetic elements of a magnetic array relative to the magnetic elements of the magnetic segment, elements of neighboring magnetic segments, and/or an environment of interest proximate to the magnetic segment are anticipated.

Further, the magnetic pole 520e could act to increase a property (e.g., a magnitude, a gradient magnitude) of the magnetic field produced by the magnetic segment 500e in the portion of subsurface vasculature 507e and to decrease a property (e.g., a magnitude, a gradient magnitude) of the magnetic field produced by the magnetic segment 500e in a region away from the body of the human 505e (i.e., to 'shield' the region below and/or to the sides of the magnetic segment 500e from the magnetic field produced by the magnetic elements 510e, 512e, 514e). Further, the magnetic pole 520e could be associated specifically with the illustrated magnetic segment 500e or could extend past the magnetic segment 500e to associate with (e.g., to be in contact with) other magnetic segments of a magnetic assembly that includes the magnetic segment 500e.

In some embodiments, the magnetic segment could have a narrowing geometry configured to concentrate a magnetic flux and/or to cause a magnetic field produced by the magnetic segment to have a specified profile (i.e., a specified pattern of field magnitude, field direction, field gradient magnitude, field gradient direction) in one or more regions relative to the magnetic segment. That is, an amount of flux and/or a magnitude of the magnetic field proximate to a narrow region of the narrowing geometry of the magnetic segment (e.g., the 'top' peak of a truncated cone) could be greater than if the geometry did not narrow (e.g., the geometry was a cylinder, rather than a truncated cone). The narrowing geometry could include a magnetic pole and/or one or more permanent magnets. The narrowing geometry could be trapezoidal, conical, pyramidal, triangular, or some other narrowing geometry.

FIG. 6A illustrates a schematic diagram of an example magnetic segment 600a comprising a magnetic flux source 610 and two magnetic poles 620a, 622a comprising a high-permeability material. The magnetic segment 600a is positioned proximate to a portion of subsurface vasculature 607a within a body of a human 605a. The magnetic flux source 610a includes at least one permanent magnet, electromagnet or other magnetic flux-producing element. The magnetic flux source 610a can additionally include magnetic poles, air gaps, sensors, mechanically actuated elements (e.g., magnetic elements or other elements mounted to gears, gimbals, servos, or other actuators), or other components. In some examples, the magnetic flux source 610a could include a single magnetic element having a magnetic moment oriented toward the portion of subsurface vasculature 607a. In some examples, the magnetic flux source 610a could include a plurality of magnetic elements having respective magnetic moments oriented to form a Halbach array.

A first magnetic pole 620a comprises a layer of the high-permeability material disposed on a side of the magnetic segment 600a opposite the human body 605a. A second (i.e., focusing) magnetic pole 622a comprises the high-permeability material disposed on a side of the magnetic segment 600a toward the human body 605a. The second magnetic pole 622a could have one of a variety of narrowing geometries such that a first cross-sectional area of the second magnetic pole 622a proximate to the magnetic flux source 610a is greater than a second cross-sectional area of the second magnetic pole 622a farther from the magnetic flux source 610a (i.e., proximate to the human body 605a).

The magnetic segment 600a could be part of a wearable device (e.g., could be one of a set of magnetic segments of a magnetic assembly) and the wearable device could further include a mount configured to mount the wearable device to an external body surface of the body of the human 605a proximate to the portion of subsurface vasculature 607a. The magnetic flux source 610a and magnetic poles 620a, 622a of the magnetic segment 600a can be configured to exert a magnetic force on magnetic particles in the portion of subsurface vasculature 607a. Further, the magnetic poles 620a, 622a could act to increase a property (e.g., a magnitude, a gradient magnitude) of the magnetic field produced by the magnetic segment 600a in the portion of subsurface vasculature 607a (e.g., proximate to a narrow end of the second magnetic pole 622a) and to decrease a property (e.g., a magnitude, a gradient magnitude) of the magnetic field produced by the magnetic segment 600a in a region away from the body of the human 605a (i.e., to 'shield' the region below the magnetic segment 600a from the magnetic field produced by the magnetic flux source 610a).

The second magnetic pole 622a could have a narrowing geometry chosen from a variety of narrowing geometries. The second magnetic pole 622a could be conical, pyramidal (e.g., a triangular pyramid, a square pyramid, a pyramid having some arbitrary polygonal base), a triangular prism, a partial ellipsoidal prism, a partial ellipsoid, or have some other narrowing or tapering geometry. The second magnetic pole 622a could have a truncated narrowing geometry (e.g., a truncated cone, a truncated pyramid, a trapezoidal prism). The second magnetic pole 622a could have a narrowing cross-sectional shape in a plane substantially perpendicular an external body surface of the human 605a proximate to which the magnetic segment 600a is positioned. For example, the second magnetic pole 622a could have a triangular cross-section, a trapezoidal cross-section, a partial elliptical cross-section, or some other narrowing shape cross-section. Further, one or both of the magnetic poles 620a, 622a could be associated specifically with the illustrated magnetic segment 600a or could extend past the magnetic segment 600a to associate with (e.g., to be in contact with) other magnetic segments of a magnetic assembly that includes the magnetic segment 600a.

Elements (e.g., 610a, 620a, 622a) of the magnetic segment 600a and/or of the composition of a magnetic assembly from a linear or other array of similar and/or different magnetic segments could have specified properties (e.g., sizes, thicknesses, widths, lengths, compositions, shapes, specified distances between segments, presence and composition of spacers disposed between segments) chosen so as to optimize certain properties of the magnetic segment and/or assembly (e.g., a magnetic field magnitude, a magnetic field gradient magnitude) given one or more constraints on the magnetic segment and/or assembly (e.g., a maximum volume, a maximum mass, a specified permanent magnet geometry). In some examples, the geometry of the second (focusing) magnetic pole 622a could be specified to maximize the magnetic field magnitude and the magnetic field gradient magnitude proximate to the second magnetic pole 622a for a given small size of magnetic flux source 610a (e.g., a small permanent (e.g., Nd52) magnet). For example, the second magnetic pole 622a could have a length of 5 millimeters, a width of 5 millimeters, a thickness of 2 millimeters, and could have a truncated pyramid geometry wherein the flat top of the truncated pyramid had a width of 1 millimeter. In some examples, the second magnetic pole 622a could have a size and/or geometry relative to other elements of the magnetic segment 600a such that the second magnetic pole 622a is magnetically saturated. Other geometries and dimensions of elements of a magnetic segment and/or assembly are anticipated.

Additionally or alternatively, one or more permanent magnets of a magnetic segment could have a narrowing geometry. FIG. 6B illustrates a schematic diagram of an example magnetic segment 600b comprising a plurality of permanent magnets 610b, 612b, 614b having respective magnetic moments (arrows) that have, together, a narrowing geometry and whose magnetic moments are oriented such that the magnetic segment forms a Halbach array. The magnetic segment 600b additionally includes a magnetic pole 620a comprising a high-permeability material. The magnetic segment 600b is positioned proximate to a portion of subsurface vasculature 607b within a body of a human 605b. The magnetic pole 620b comprises a layer of the high-permeability material disposed on a side of the magnetic segment 600b opposite the human body 605b. The permanent magnets 610b, 612b, 614b could have one of a variety of narrowing geometries such that a cross-sectional shape of the permanent magnets 610b, 612b, 614b in a plane substantially perpendicular to an external body surface of the body of the human 605b proximate to the portion of subsurface vasculature 607b was narrower proximate to the external body surface.

The magnetic assembly 600b could be part of a wearable device (e.g., could be one of a set of magnetic segments of a magnetic assembly) and the wearable device could further include a mount configured to mount the wearable device to an external body surface of the body of the human 605b proximate to the portion of subsurface vasculature 607b. The permanent magnets 610b, 612b, 614b of the magnetic segment 600b can be configured to exert a magnetic force on magnetic particles in the portion of subsurface vasculature 607b. The permanent magnets 610b, 612b, 614b being arranged as a Halbach array comprises the orientation of the magnetic moment of an individual permanent magnet being substantially perpendicular to (i.e., rotated approximated ninety degrees relative to) the magnetic moments of permanent magnets in the array adjacent to the individual permanent magnet and substantially antiparallel to (i.e., rotated approximated 180 degrees relative to) permanent magnets in the array that are adjacent to the permanent magnets that are adjacent to the individual permanent magnet. Other arrangements of the magnetic moments of permanent magnets of a magnetic array relative to the permanent magnets of the magnetic segment, elements of neighboring magnetic segments, and/or an environment of interest proximate to the magnetic assembly are anticipated.

Further, the magnetic pole 620b could act to increase a property (e.g., a magnitude, a gradient magnitude) of the magnetic field produced by the magnetic segment 600b in the portion of subsurface vasculature 607b and to decrease a property (e.g., a magnitude, a gradient magnitude) of the magnetic field produced by the magnetic segment 600b in a region away from the body of the human 605b (i.e., to 'shield' the region below the magnetic segment 600b from the magnetic field produced by the permanent magnets 610b, 612b, 614b). Further, the magnetic pole 620b could be associated specifically with the illustrated magnetic segment 600b or could extend past the magnetic segment 600b to associate with (e.g., to be in contact with) other magnetic segments of a magnetic assembly that includes the magnetic segment 600b.

The permanent magnets 610b, 612b, 614b could have a narrowing geometry chosen from a variety of narrowing geometries. The permanent magnets 610b, 612b, 614b could be conical, pyramidal (e.g., a triangular pyramid, a square pyramid, a pyramid having some arbitrary polygonal base), a triangular prism, a partial ellipsoidal prism, a partial ellipsoid, or have some other narrowing or tapering geometry. The permanent magnets 610b, 612b, 614b could have a truncated narrowing geometry (e.g., a truncated cone, a truncated pyramid, a trapezoidal prism). The permanent magnets 610b, 612b, 614b could have a narrowing cross-sectional shape in a plane substantially perpendicular an external body surface of the human 605b proximate to which the magnetic segment 600b is positioned. For example, the permanent magnets 610b, 612b, 614b could have a triangular cross-section, a trapezoidal cross-section, a partial elliptical cross-section, or some other narrowing shape cross-section.

FIG. 7 illustrates a schematic diagram of an example magnetic segment 700 comprising a magnetic pole 720 and a plurality of magnetic elements 710, 712, 714, 716 having respective magnetic moments (arrows). The magnetic segment 700 is positioned proximate to a portion of subsurface vasculature 707 within a body of a human 705. The magnetic segment 700 could be part of a wearable device (e.g., could be one of a set of magnetic segments of a magnetic assembly) and the wearable device could further include a mount configured to mount the wearable device to an external body surface of the body of the human 705 proximate to the portion of subsurface vasculature 707. The magnetic segment 700 partially encloses a portion of the body of the human 707; that is, the magnetic elements 710, 712, 714, 716 are disposed on a concave surface of the magnetic segment 700 and the concave surface is configured to partially enclose a convex surface (i.e., the external body surface) of the human 707.

The magnetic pole 720 is configured to increase a property (e.g., a magnitude, a gradient magnitude) of the magnetic field produced by the magnetic segment 700 in the portion of subsurface vasculature 707 and to decrease a property (e.g., a magnitude, a gradient magnitude) of the magnetic field produced by the magnetic segment 700 in a region away from the body of the human 705 (i.e., to 'shield' the region below the magnetic segment 700 from the magnetic field produced by the magnetic elements 710, 712, 714, 716). Further, the magnetic pole 720 could be associated specifically with the illustrated magnetic segment 700 or could extend past the magnetic segment 700 to associate with (e.g., to be in contact with) other magnetic segments of a magnetic assembly that includes the magnetic segment 700. First 710 and third 714 magnetic elements have magnetic moments pointing into respective proximate regions of the external body surface of the human 705 and third 712 and fourth 716 magnetic elements have magnetic moments pointing away from respective proximate regions of the external body surface of the human 705.

In some embodiments, the magnetic segment could have magnetic elements (and magnetic moments thereof) configured according to a cylindrical, a spherical, an ellipsoidal, or some other three-dimensional geometry configured to produce a magnetic flux and/or to cause a magnetic field produced by the magnetic segment to have a specified profile (i.e., a specified pattern of field magnitude, field direction, field gradient magnitude, field gradient direction) in one or more regions relative to the magnetic segment. That is, while certain configurations of magnetic segments described herein (e.g., 100a, 200a, 200b, 400a, 400b, 40c, 400d, 500a, 500b, 500c, 500d, 500e, 600b, 700) include magnetic elements having substantially planar configurations, magnetic elements and/or other components of a magnetic segment of a magnetic assembly (e.g., stacked magnetic segments arranged in a linear array) could be configured in other ways.

Figure 8A:
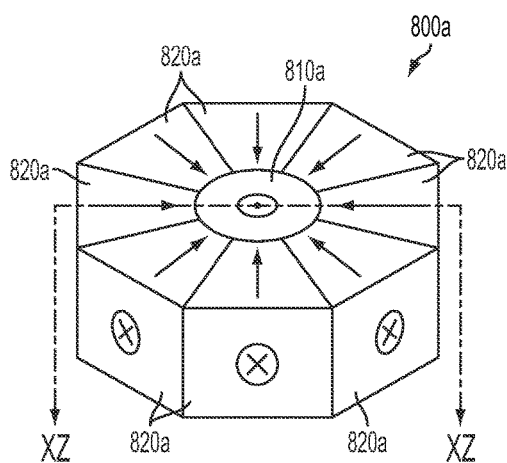
FIG. 8A is perspective view of an example magnetic segment.

FIG. 8A illustrates a perspective view of an example magnetic segment 800a having an axial magnetic element 810a and a plurality of radial magnetic elements 820a. The axial magnetic element 810a has a magnetic moment directed upward (illustrated by the dot-in-circle symbol to indicate that the magnetic moment is directed out of the illustrated surface of the axial magnetic element 810a), parallel to a central axis of the axial magnetic element 810a. The radial magnetic elements 820b are disposed proximate to and surrounding the axial magnetic element 810a and have respective magnetic moments oriented toward the central axis of the axial magnetic element 810a (illustrated by arrows and by the cross-in-circle symbol to indicate that the magnetic moment is directed into the illustrated surfaces of the radial magnetic elements 820a).

Figure 8B:
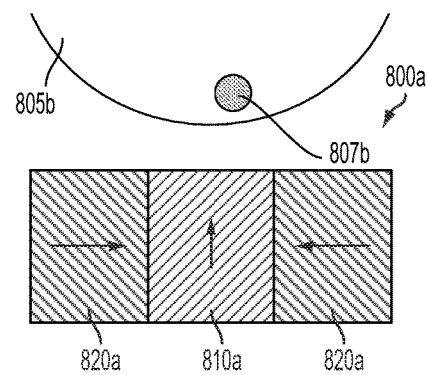
FIG. 8B is cross-sectional view of the example magnetic segment illustrated in FIG. 8A.

FIG. 8B illustrates a cross-sectional schematic diagram of the example magnetic segment 800a taken though plane XZ illustrated in FIG. 8A. The magnetic moments of the axial magnetic element 810a and two radial magnetic elements 820a are shown (arrows). The magnetic segment 800a is positioned proximate to a portion of subsurface vasculature 807a within a body of a human 805a. The magnetic segment 800a could be part of a wearable device (e.g., could be one of a set of magnetic segments of a magnetic assembly) and the wearable device could further include a mount configured to mount the wearable device to an external body surface of the body of the human 805a proximate to the portion of subsurface vasculature 807a.

The number, shape, disposition, and other properties of the magnetic segment 800a are intended as a non-limiting example of a magnetic segment having elements (e.g., magnetic elements having respective magnetic moments) disposed in three dimensions. Other such magnetic segments are anticipated. Further, the overall shape of such magnetic segments could be flattened (e.g., the shape of individual radial magnetic elements could vary such that the magnetic segment had an overall flatter shape) such that such magnetic segments could be tightly packed into a space (e.g., into a magnetic assembly). More or fewer radial magnetic elements could be included. A magnetic segment could include multiple rings or row of radial magnetic elements (e.g., the example magnetic segment 800a could further include an outside ring of magnetic elements having respective magnetic moments oriented, e.g., antiparallel to the magnetic moment of the axial magnetic segment 810a) or additional magnetic elements formed, disposed, or otherwise configured according to some other design.

Figure 8C:
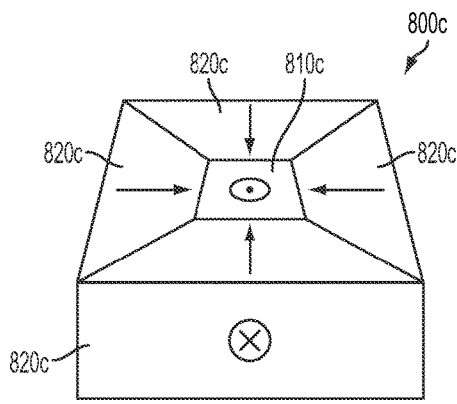
FIG. 8C is perspective view of an example magnetic segment.

For example, FIG. 8C illustrates a perspective view of an example magnetic segment 800c having a square-shaped axial magnetic element 810b and four trapezoidally-shaped radial magnetic elements 820b. The axial magnetic element 810b has a magnetic moment directed upward (illustrated by the dot-in-circle symbol to indicate that the magnetic moment is directed out of the illustrated surface of the axial magnetic element 810b), parallel to a central axis of the axial magnetic element 810b. The radial magnetic elements 820b are disposed proximate to and surrounding the axial magnetic element 810a and have respective magnetic moments oriented toward the central axis of the axial magnetic element 810a (illustrated by arrows and by the cross-in-circle symbol to indicate that the magnetic moment is directed into the illustrated surface of the radial magnetic elements 820b).

Figure 8D:
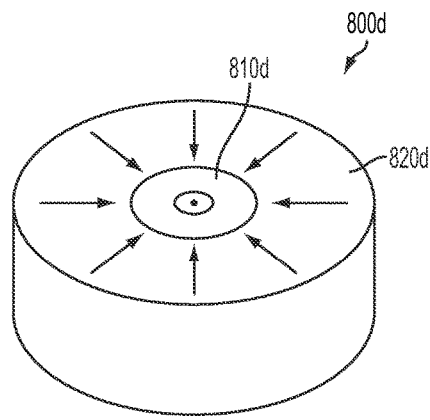
FIG. 8D is perspective view of an example magnetic segment.

In another example, FIG. 8D illustrates a perspective view of an example magnetic segment 800d having a cylindrical axial magnetic element 810d and a ring-shaped radial magnetic element 820d. The axial magnetic element 810d has a magnetic moment directed upward (illustrated by the dot-in-circle symbol to indicate that the magnetic moment is directed out of the illustrated surface of the axial magnetic element 810d), parallel to a central axis of the axial magnetic element 810d. The radial magnetic element 820d is disposed proximate to and surrounding the axial magnetic element 810d and magnetic domains of the radial magnetic element 820d are configured such that local magnetic moments of regions within the radial magnetic element 820d are oriented toward the central axis of the axial magnetic element 810a (arrows). The radial magnetic element 820d could be configured in this way by adhering or otherwise forming together a plurality of magnetic elements (e.g., a plurality of thin, truncated-wedge-shaped slices of magnetized magnetic material), by manipulating the orientation of the magnetic moment of magnetic domains within a single ring-shaped piece of magnetic material, or by some other method(s).

Magnetic assemblies, magnetic segments, devices containing magnetic segments and/or assemblies, magnetic particles, and other aspects and embodiments described herein (e.g., 100a, 200a, 200b, 200c, 370a, 370b, 400a, 400b, 400c, 400d, 500a, 500b, 500c, 500d, 500e, 600a, 600b, 700, 800a, 800c, 800d) could be configured and/or operated to provide a variety of applications. In some examples, magnetic particles could be configured to bind to an analyte of interest, and a magnetic assembly (e.g., a magnetic assembly including a linear or other array of magnetic segments) could be configured to collect or otherwise manipulate the magnetic particles to enable the detection, extraction, modification, or other manipulation of the analyte. For example, a detector could be disposed proximate to a magnetic assembly that is configured to collect the magnetic particles, and the detector could detect one or more properties of the analyte bound to the magnetic particles (e.g., by detecting an optical property of the analyte and/or magnetic particles (e.g., fluorescent detection of a fluorophore), by detecting a magnetic property of the magnetic particles). Additionally or alternatively, an energy emitter could be disposed proximate to the magnetic assembly, and the energy emitter could emit energy toward the collected magnetic particles sufficient to alter one or more properties of the analyte (e.g., to destroy, denature, heat, change a conformation state of, other otherwise modify the analyte). In some examples, collection of an analyte bound to magnetic particles by a magnetic assembly could enable the extraction of the analyte and magnetic particles (e.g., using a hypodermic needle).

In some applications, manipulation of magnetic particles could enable detection and/or modification of an analyte. For example, the reaction (e.g., a differential and/or absolute motion) of a magnetic particle to a magnetic field generated by a magnetic assembly and/or magnetic segments thereof (e.g., 100a, 200a, 200b, 200c, 370a, 370b, 400a, 400b, 400c, 400d, 500a, 500b, 500c, 500d, 500e, 600a, 600b, 700, 800a, 800c, 800d) could be detected, and one or more properties of the reaction could be used to determine one or more properties of the magnetic particle. For example, the degree change in velocity of a magnetic particle, when exposed to the magnetic field of the magnetic assembly, could be related to whether the magnetic particle was bound to an analyte. In some examples, the magnetic particles could be configured to couple an oscillating electromagnetic field into an increase in heat proximate to the magnetic particle, and this increase in heat could be used to detect one or more properties of the magnetic particle and/or to modify the environment proximate to the particle (e.g., to denature an analyte bound to the magnetic particle). Other configurations, operations, and applications of the embodiments described herein are anticipated.

V. Example Methods

Figure 9:
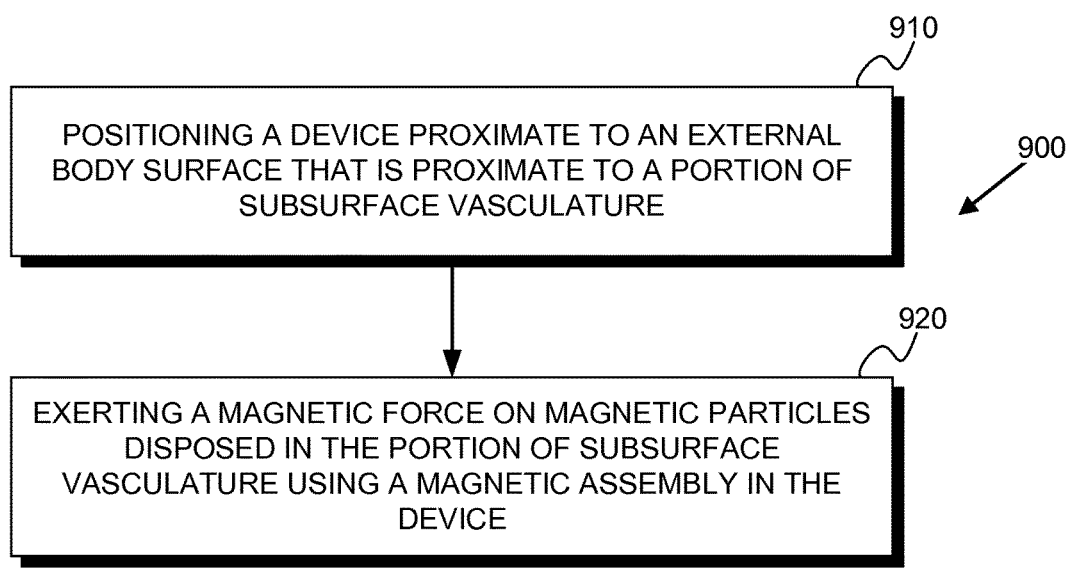
FIG. 9 is a flowchart of an example method

FIG. 9 is a flowchart of an example method 900 for exerting a magnetic force on magnetic particles using a device. The device includes a magnetic assembly that includes a plurality of magnetic segments arranged in a linear array and separated from each other by respective specified distances. Each magnetic segment of the magnetic assembly includes one or more magnetic elements each having a respective magnetic moment. Further, the plurality of magnetic segments includes a first magnetic segment that is next to a second magnetic segment; magnetic moments of respective first and second magnetic elements of the first magnetic segment are each oriented antiparallel to the magnetic moments of respective corresponding first and second magnetic elements of the second magnetic segment. The magnetic assembly and/or magnetic segments thereof could be configured as described herein (e.g., 100a, 200a, 200b, 200c, 370a, 370b, 400a, 400b, 400c, 400d, 500a, 500b, 500c, 500d, 500e, 600a, 600b, 700, 800a, 800c, 800d) or in some other way according to an application.

The method 900 includes positioning the device onto the external surface proximate to the portion of subsurface vasculature 910. This could include operating a mount included in the device that is configured to enclose a portion of the body of a user (e.g., a wrist, an ankle, a chest) to secure the magnetic assembly at a specified location relative to the portion of subsurface vasculature. In some examples, this could include positioning the magnetic device relative to a visible or other landmark on or beneath the external body surface (e.g., a tattoo, a visible artery or vein, bony protuberance, a joint, a birth mark). In some examples, this could include manipulating and/or changing the location of the device relative to some indication from the device, e.g., and indication from the device that the magnetic assembly and/or a magnetic segment thereof is located proximate to the portion of subsurface vasculature.

The method 900 additionally includes exerting a magnetic force on magnetic particles disposed in the portion of subsurface vasculature using the magnetic assembly disposed in the device 920. This could include exerting an attractive force on the magnetic particles sufficient to collect the magnetic particles in the portion of subsurface vasculature. This could include exerting a magnetic force having a direction substantially parallel to a direction of blood flow in the portion of subsurface vasculature. Other examples of exerting a magnetic force on magnetic particles using the device and applications thereof are anticipated. Further, exerting a magnetic force 920 could include applying a voltage and/or current to any magnetic elements of the plurality of magnetic elements of the device that are electromagnets.

The method 900 could include additional steps or elements. For example, the method 900 could include introducing the magnetic particles into the portion of subsurface vasculature (e.g., injecting, ingesting, transdermally transferring, or otherwise introducing the engineered particles into a lumen of vasculature of a human). In some examples, the magnetic particles could be configured to bind to an analyte and to enable detection of one or more properties of, modification of one or more properties of (e.g., by emitting energy from an energy emitter of the device into the portion of subsurface vasculature), and/or some other interaction with the analyte.

In some examples, the method 900 could include detecting one or more properties of an analyte to which the magnetic particles are configured to bind. This could include operating a detector of the device to detect the one or more properties of the bound analyte. In some examples, this could include exerting an attractive magnetic force on the magnetic particles such that the magnetic particles and instances of the analyte bound thereto are caused to collect in a portion of subsurface vasculature proximate to the magnetic assembly and/or the detector of the device. In some examples, this could include exerting a first magnetic force on first magnetic particles that are bound to the analyte and exerting a second magnetic force on second magnetic particles that are not bound to the analyte such that the first and second magnetic particles are separated such that a detector of the device substantially only detects one or more properties of the first set of magnetic particles. Other methods of detecting one or more properties of an analyte using a magnetic assembly disposed in a device positioned proximate to a portion of subsurface vasculature are anticipated.

In some examples, the method 900 could include altering a clearance rate (i.e., a rate at which a substance is removed from an environment) of an analyte out of the portion of subsurface vasculature and/or out of some other region of a user's body (e.g., out of the blood of the user) using the magnetic assembly of the device. This could include exerting an attractive magnetic force on magnetic particles disposed in the portion of subsurface vasculature that are configured to bind to the analyte. The attractive magnetic force could be sufficient to collect the magnetic particles and instances of the analyte bound thereto in the portion of subsurface vasculature proximate to the device. Collection of the magnetic particles configured to bind to the analyte act to alter (e.g., to reduce) a rate of clearance of the analyte from the body of the user (e.g., by collecting the analyte in the portion of subsurface vasculature such that less of the analyte is available to be cleared from the body of the user by e.g., kidneys of the user). Other methods of using the device and/or magnetic particles to affect a clearance rate, a reaction rate, a rate of decomposition and/or deactivation, an effectiveness, a chemical activity, or some other property or properties of an analyte are anticipated.

VI. Example Wearable Devices

Figure 10:
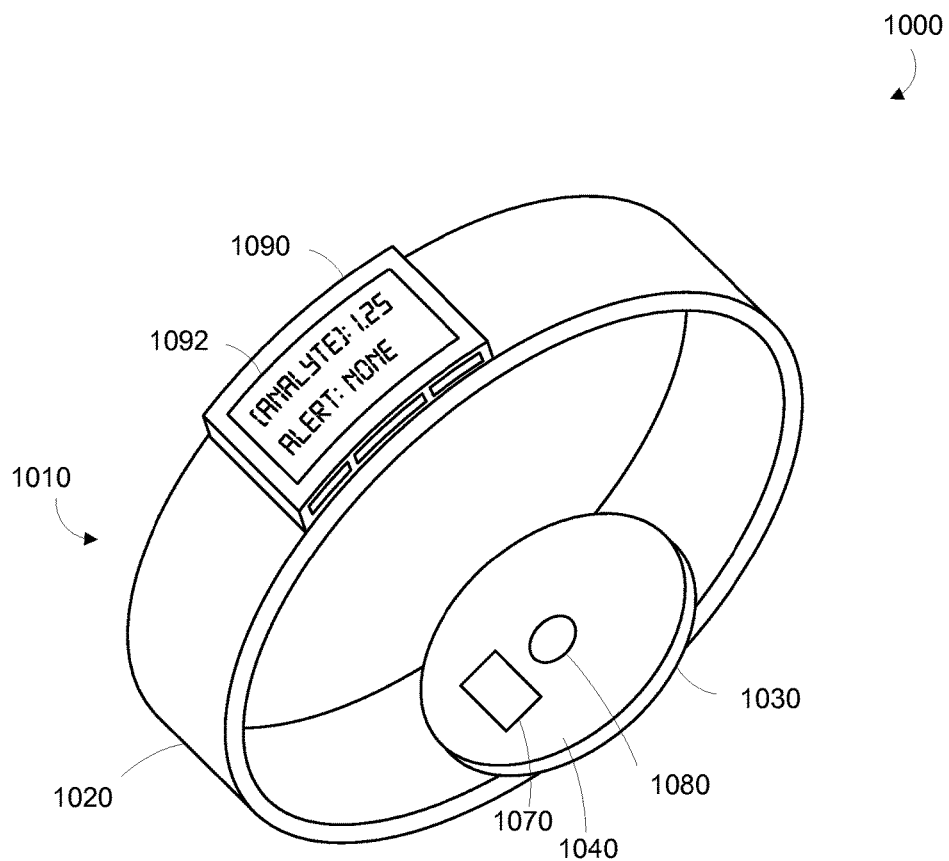
FIG. 10 is a perspective view of an example wearable device.

A wearable device 1000 can measure a plurality of physiological parameters of a person wearing the device, among other functions. Some or all of the functions of the wearable device 1000 are enabled by collection, separation, or some other manipulation of magnetic particles in blood of the wearer of the device. Such manipulations can be effected by the exertion of magnetic forces on the magnetic particles by a magnetic assembly and/or magnetic segments thereof (e.g., 100a, 200a, 200b, 200c, 370a, 370b, 400a, 400b, 400c, 400d, 500a, 500b, 500c, 500d, 500e, 600a, 600b, 700, 800a, 800c, 800d) disposed on or in the wearable device 1000. The term "wearable device," as used in this disclosure, refers to any device that is capable of being worn at, on or in proximity to a body surface, such as a wrist, ankle, waist, chest, or other body part. In order to manipulate magnetic particles and/or take in vivo measurements in a non-invasive manner from outside of the body, the wearable device may be positioned on a portion of the body where subsurface vasculature containing magnetic particles is easily affectable (e.g., by exertion of magnetic forces) and observable, depending on the type of modification and detection systems used. The device may be placed in close proximity to the skin or tissue, but need not be touching or in intimate contact therewith. A mount 1010, such as a belt, wristband, ankle band, etc. can be provided to mount the device at, on or in proximity to the body surface. The mount 1010 may prevent the wearable device 1000 from moving relative to the body to ensure effective manipulation of magnetic particles and/or detection of one or more physiological properties of the wearer. In one example, shown in FIG. 10, the mount 1010, may take the form of a strap or band 1020 that can be worn around a part of the body. Further, the mount 1010 may include an adhesive material for adhering the wearable device 1000 to the body of a wearer.

A manipulation platform 1030 is disposed on the mount 1010 such that it can be positioned on the body where subsurface vasculature is easily affected. An inner face 1040 of the manipulation platform 1030 is intended to be mounted facing to the body surface. The manipulation platform 1030 may house a magnetic assembly 1080. In such embodiments, the magnetic assembly 1080 could be configured to separate collect, separate, or otherwise manipulate particles in a portion of subsurface vasculature by exerting magnetic forces on the magnetic particles. The magnetic assembly 1080 could include electromagnets, permanent magnets, magnetic segments, spacers, magnetic shims, or other magnetic or non-magnetic material configured in a variety of ways (e.g., configured similarly to magnetic assemblies and/or magnetic segments thereof (e.g., 100a, 200a, 200b, 200c, 370a, 370b, 400a, 400b, 400c, 400d, 500a, 500b, 500c, 500d, 500e, 600a, 600b, 700, 800a, 800c, 800d)).

In some examples, the wearable device 1000 further includes at least one detector 1070 for detecting at least one physiological parameter, which could include any parameters that may relate to the health of the person wearing the wearable device. For example, the detector 1070 could be configured to measure blood pressure, pulse rate, respiration rate, skin temperature, etc. At least one of the detectors 1070 could be configured to non-invasively measure one or more properties of magnetic particles in blood and/or analytes bound thereto circulating in subsurface vasculature proximate to the wearable device. In a non-exhaustive list, detector 1070 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., RF, magnetic resonance) sensor. Operation of the detector 1070 could be related to and/or contingent on collection, separation, or some other manipulation of magnetic particles by the magnetic assembly 1080.

The wearable device 1000 may also include a user interface 1090 via which the wearer of the device may receive one or more recommendations or alerts generated from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 1090 may include a display 1092 where a visual indication of the alert or recommendation may be displayed. The display 1092 may further be configured to provide an indication the battery status of the device or the status of the modification system or an indication of any measured physiological parameters, for instance, the concentrations of certain blood analytes being measured.

Figure 11A:
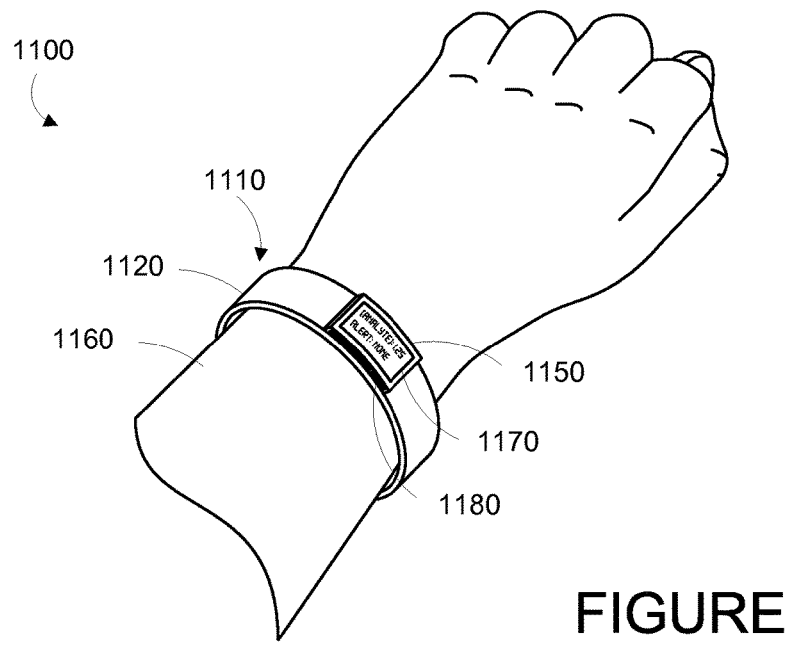
FIG. 11A is a perspective top view of an example wrist-mounted device, when mounted on a wearer's wrist.
Figure 11B:
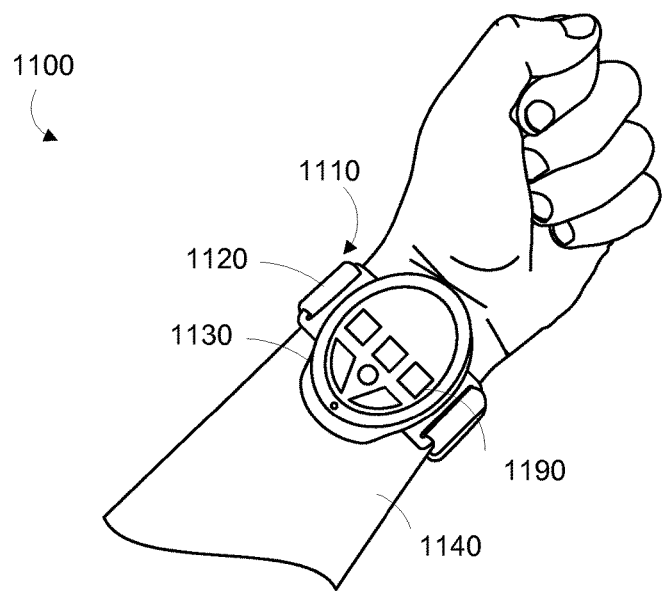
FIG. 11B is a perspective bottom view of the example wrist-mounted device shown in FIG. 11A, when mounted on a wearer's wrist.

In one example, the wearable device is provided as a wrist-mounted device, as shown in FIGS. 11A and 11B. The wrist-mounted device may be mounted to the wrist of a living subject with a wristband or cuff, similar to a watch or bracelet. As shown in FIGS. 11A and 11B, the wrist mounted device 1100 may include a mount 1110 in the form of a wristband 1120, a manipulation platform 1130 positioned on the anterior side 1140 of the wearer's wrist, and a user interface 1150 positioned on the posterior side 1160 of the wearer's wrist. The wearer of the device may receive, via the user interface 1150, one or more recommendations or alerts generated either from a remote server or other remote computing device, or alerts based on physiological properties of a wearer detected by the wrist-mounted device 1100. Such a configuration may be perceived as natural for the wearer of the device in that it is common for the posterior side 1160 of the wrist to be observed, such as the act of checking a wrist-watch. Accordingly, the wearer may easily view a display 1170 on the user interface. Further, the manipulation platform 1130 may be located on the anterior side 1140 of the wearer's wrist where the subsurface vasculature may be readily affectable. However, other configurations are contemplated.

The display 1170 may be configured to display a visual indication of the alert or recommendation and/or an indication of the status of the wearable device and an indication of measured physiological parameters, for instance, the concentrations of certain target blood analytes bound to collected, separated, or otherwise magnetically manipulated magnetic particles in the blood. Further, the user interface 1150 may include one or more buttons 1180 for accepting inputs from the wearer. For example, the buttons 1180 may be configured to change the text or other information visible on the display 1170. As shown in FIG. 11B, manipulation platform 1130 may also include one or more buttons 1190 for accepting inputs from the wearer. The buttons 1190 may be configured to accept inputs for controlling aspects of the wrist-mounted device 1100, such as inputs indicating the wearer's current health state (i.e., normal, migraine, shortness of breath, heart attack, fever, "flu-like" symptoms, food poisoning, etc.).

VII. Conclusion

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

While various aspects and embodiments herein are described in connection with exerting forces on magnetic particles disposed in a portion of subsurface vasculature, other applications and environments are possible. Aspects and embodiments herein could be applied to exert forces on magnetic particles in in vivo or in vitro human or animal tissues, a fluid in a scientific, medical, or industrial testing process, or some other environment. Magnetic forces could be exerted on magnetic particles disposed in a natural environment, e.g., a lake, river, stream, marsh, or other natural locale. Magnetic forces could be exerted on magnetic particles disposed in a fluid environment of an industrial process or other artificial environment, e.g., a water treatment process, a food preparation process, a pharmaceutical synthesis process, a chemical synthesis process, a brewing and/or distilling process, or other artificial locale. Magnetic forces could be exerted on magnetic particles disposed in an environment that includes a flowing fluid (e.g., fluid flowing in a blood vessel, a pipe, a culvert) and/or a substantially static fluid. Other environments and applications of aspects and embodiments described herein are anticipated.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

What is claimed is:

1. A device comprising: a magnetic assembly comprising a plurality of magnetic segments, wherein the plurality of magnetic segments are arranged in a linear array, wherein the magnetic segments are separated from each other by respective specified distances, wherein each magnetic segment comprises two or more magnetic elements each having a respective magnetic moment, wherein the magnetic assembly is configured to be positioned proximate to an external body surface such that the magnetic assembly exerts a magnetic force on magnetic particles in a portion of subsurface vasculature proximate to the external body surface, wherein a first magnetic segment of the plurality of magnetic segments is next to a second magnetic segment of the plurality of magnetic segments, and wherein the magnetic moments of respective first and second magnetic elements of the first magnetic segment are each oriented antiparallel to the magnetic moments of respective corresponding first and second magnetic elements of the second magnetic segment, wherein the magnetic particles are configured to bind to an analyte;

and a detector, wherein the detector is configured to detect one or more properties of the analyte bound to the magnetic particles, or an energy emitter, wherein the energy emitter is configured to emit energy into the subsurface vasculature sufficient to alter one or more properties of the analyte bound to the magnetic particles.

2. The device of claim 1, wherein the magnetic force is an attractive magnetic force, and wherein the attractive magnetic force is sufficient to collect the magnetic particles in the portion of subsurface vasculature proximate to the magnetic assembly.

3. The device of claim 1, wherein the magnetic particles include first magnetic particles and second magnetic particles, wherein the magnetic assembly exerts a magnetic force on magnetic particles that are disposed in the portion of subsurface vasculature including a first magnetic force on the first magnetic particles and a second magnetic force on the second magnetic particles, and wherein the first magnetic force and the second magnetic force are sufficiently different to cause separation of the first magnetic particles and the second magnetic particles.

4. The device of claim 1, wherein the first magnetic segment of the magnetic assembly comprises a first magnetic element having a first magnetic moment oriented substantially into the external body surface when positioned proximate the external body surface.

5. The device of claim 4, wherein the first magnetic segment of the magnetic assembly comprises at least three magnetic elements, wherein the first magnetic element of the at least three magnetic elements is adjacent to a second magnetic element of the at least three magnetic elements, wherein the second magnetic element is adjacent to a third magnetic element of the at least three magnetic elements, wherein the second and third magnetic elements have respective second and third magnetic moments, wherein the second magnetic moment is substantially perpendicular to the first magnetic moment, wherein the third magnetic moment is substantially perpendicular to the second magnetic moment, wherein the third magnetic moment is substantially antiparallel to the first magnetic moment.

6. The device of claim 5, wherein the at least three magnetic elements are permanent magnets, and wherein the at least three magnetic elements have a cross-sectional shape in a plane substantially perpendicular to a long axis of the linear array of magnetic segments, wherein the cross-sectional shape is narrower proximate to the external body surface.

7. The device of claim 5, wherein the first magnetic segment of the magnetic assembly comprises three magnetic elements, wherein the second magnetic moment is configured to be oriented substantially into the external body surface, and wherein the first magnetic segment further comprises: a layer of high-permeability material, wherein the layer of high-permeability material partially encloses the three magnetic elements, wherein the layer of high-permeability material is disposed on a first side of the three magnetic elements of the magnetic assembly, wherein the first side is configured to be an opposite side of the three magnetic elements from the external body surface, wherein the layer of high-permeability material is disposed on a side of the third magnetic element opposite the second magnetic element, and wherein the layer of high-permeability material is disposed on a side of the first magnetic element opposite the second magnetic element.

8. The device of claim 5, wherein the first magnetic segment of the magnetic assembly comprises an axial magnetic element having a magnetic moment configured to be oriented substantially into the external body surface, wherein the axial magnetic element has a central axis parallel to the magnetic moment of the axial magnetic element, wherein the first magnetic segment further comprises a plurality of radial magnetic elements having respective magnetic moments oriented toward the central axis, and wherein the plurality of radial magnetic elements are disposed proximate to and surrounding the axial magnetic element.

9. The device of claim 1, wherein the first magnetic segment of the magnetic assembly further comprises a focusing pole comprised of high-permeability material, wherein the focusing pole is disposed on a first side of the first magnetic segment, wherein the first side is a side of the first magnetic segment configured to be proximate the external body surface, wherein the focusing pole has a first cross-sectional area proximate to the first side of the first magnetic segment, wherein the focusing pole has a second cross-sectional area farther from the first side of the first magnetic segment, and wherein the second cross-sectional area is less than the first cross-sectional area.

10. The device of claim 1, further comprising a spacer comprised of a low-permeability material, wherein the spacer is disposed between the first and second magnetic segments.

11. The device of claim 1, wherein the magnetic assembly has a first side configured to be proximate the external body surface and a second side opposite the first side, and wherein the magnetic assembly comprises a layer of high-permeability material disposed on the second side.

12. The device of claim 1, wherein the magnetic assembly has a concave surface, the external body surface has a convex surface, and the concave surface is configured to at least partially enclose the convex surface, and wherein at least two magnetic elements of the two or more magnetic elements of the first magnetic segment are disposed on the concave surface.

13. The device of claim 12, wherein the first magnetic segment comprises four magnetic elements disposed on the concave surface, wherein each of the four magnetic elements has a respective magnetic moment that is configured to be substantially perpendicular to a respective local external body surface, wherein a first magnetic element of the four magnetic elements has a magnetic moment configured to be pointing into the respective local external body surface, wherein a second magnetic element of the four magnetic elements has a magnetic moment pointing configured to be away from the respective local external body surface, wherein the second magnetic element is proximate to the first magnetic element, wherein a third magnetic element of the four magnetic elements has a magnetic moment configured to be pointing into the respective local external body surface, wherein the third magnetic element is proximate to the second magnetic element, wherein the third magnetic element is disposed opposite the first magnetic element relative to the second magnetic element, wherein the magnetic moment of the third magnetic element is substantially antiparallel to the magnetic moment of the second magnetic element, wherein a fourth magnetic element of the four magnetic elements has a magnetic moment configured to be pointing away from the respective local external body surface, wherein the fourth magnetic element is proximate to the third magnetic element, wherein the fourth magnetic element is disposed opposite the second magnetic element relative to the third magnetic element, and wherein the first magnetic segment further comprises: a layer of high-permeability material, wherein the layer of high-permeability material has a concave shape, wherein the four magnetic elements have respective first sides configured to be proximate the respective local external body surfaces, wherein the four magnetic elements have respective second sides opposite the respective first sides, and wherein the layer of high-permeability material is disposed on the respective second sides.

14. A method, comprising: positioning a device comprising a magnetic assembly proximate to an external body surface that is proximate to a portion of subsurface vasculature, wherein the magnetic assembly comprises a plurality of magnetic segments, wherein the plurality of magnetic segments are arranged in a linear array, wherein the magnetic segments are separated from each other by respective specified distances, wherein each magnetic segment comprises two or more magnetic elements each having a respective magnetic moment, wherein a first magnetic segment of the plurality of magnetic segments is next to a second magnetic segment of the plurality of magnetic segments, and wherein the magnetic moments of respective first and second magnetic elements of the first magnetic segment are each oriented antiparallel to the magnetic moments of respective corresponding first and second magnetic elements of the second magnetic segment; and exerting, by the magnetic assembly in the positioned device, a magnetic force on magnetic particles disposed in the portion of subsurface vasculature.

15. The method of claim 14, further comprising introducing the magnetic particles into the portion of subsurface vasculature.

16. The method of claim 14, wherein the magnetic particles are configured to bind to an analyte, wherein the device further comprises an energy emitter configured to emit energy into the portion of subsurface vasculature, wherein exerting a magnetic force onto the magnetic particles comprises exerting an attractive magnetic force, wherein the attractive magnetic force is sufficient to collect the magnetic particles in the portion of subsurface vasculature proximate to the magnetic assembly, and further comprising:
    emitting energy into the portion of subsurface vasculature, wherein the energy emitted into the portion of subsurface vasculature is sufficient to modify one or more properties of the analyte bound to the magnetic particles that are disposed in the portion of subsurface vasculature.

17. The method of claim 14, wherein the magnetic particles are configured to bind to an analyte, wherein the analyte has a biological effect, wherein the analyte has a first rate of clearance, wherein the first rate of clearance is a rate of transport of the analyte out of the portion of subsurface vasculature when the device is not disposed on the external body surface proximate to the portion of subsurface vasculature, wherein exerting a magnetic force onto magnetic particles that are disposed in the portion of subsurface vasculature comprises exerting an attractive magnetic force, wherein the attractive magnetic force is sufficient to collect the magnetic particles in the portion of subsurface vasculature proximate to the magnetic assembly, wherein the analyte has a second rate of clearance, wherein the second rate of clearance is a rate of transport of the analyte out of the portion of subsurface vasculature when the device is disposed on the external body surface proximate to the portion of subsurface vasculature such that the magnetic assembly of the device exerts an attractive magnetic force on the magnetic particles sufficient to collect the magnetic particles in the portion of subsurface vasculature proximate to the magnetic assembly, and wherein the second rate of clearance is less than the first rate of clearance.

18. The method of claim 14, wherein the magnetic particles are configured to bind to an analyte, wherein the device further comprises a detector configured to detect one or more properties of the analyte bound to the magnetic particles that are disposed in the portion of subsurface vasculature, wherein exerting a magnetic force onto the magnetic particles comprises exerting an attractive magnetic force, wherein the attractive magnetic force is sufficient to collect the magnetic particles in the portion of subsurface vasculature proximate to the magnetic assembly, and further comprising:
    detecting one or more properties of the analyte bound to the magnetic particles that are disposed in the portion of subsurface vasculature.

* * * * *